(12) United States Patent
Binder et al.

(10) Patent No.: US 9,090,579 B2
(45) Date of Patent: Jul. 28, 2015

(54) PROCESSES FOR MAKING SUGAR AND/OR SUGAR ALCOHOL DEHYDRATION PRODUCTS

(71) Applicant: ARCHER DANIELS MIDLAND COMPANY, Decatur, IL (US)

(72) Inventors: Thomas P. Binder, Decatur, IL (US); Alexandra Sanborn, Lincoln, IL (US)

(73) Assignee: Archer Daniels Midland Co., Decatur, IL (US)

( * ) Notice: Subject to any disclaimer, the term of this patent is extended or adjusted under 35 U.S.C. 154(b) by 0 days.

(21) Appl. No.: 14/379,642

(22) PCT Filed: Mar. 7, 2013

(86) PCT No.: PCT/US2013/029579
§ 371 (c)(1),
(2) Date: Aug. 19, 2014

(87) PCT Pub. No.: WO2013/138153
PCT Pub. Date: Sep. 19, 2013

(65) Prior Publication Data
US 2015/0005516 A1  Jan. 1, 2015

Related U.S. Application Data

(60) Provisional application No. 61/609,401, filed on Mar. 12, 2012, provisional application No. 61/619,976, filed on Apr. 4, 2012.

(51) Int. Cl.
C07D 307/02 (2006.01)
C07D 307/46 (2006.01)
C07D 493/04 (2006.01)
C07D 307/48 (2006.01)
C07D 307/50 (2006.01)
C07H 3/02 (2006.01)

(52) U.S. Cl.
CPC ............ *C07D 307/46* (2013.01); *C07D 307/48* (2013.01); *C07D 307/50* (2013.01); *C07D 493/04* (2013.01); *C07H 3/02* (2013.01)

(58) Field of Classification Search
CPC .. C07D 493/04; C07D 307/46; C07D 307/48; C07D 307/50; C07H 3/02
USPC ........................................................ 549/488
See application file for complete search history.

(56) References Cited

U.S. PATENT DOCUMENTS 7,572,925 B2 * 8/2009 Dumesic et al. .............. 549/488

OTHER PUBLICATIONS

James, Towards the conversion of carbohydrate biomass feedstocks to biofuels via Hydroxylmethylfurfural, Energy & Environmental Science, 2010,3, p. 1833-1850.*

* cited by examiner

*Primary Examiner* — T. Victor Oh
(74) *Attorney, Agent, or Firm* — William B. Miller

(57) ABSTRACT

A process is disclosed for making dehydration products from an aqueous sugars solution including pentoses, hexoses or both, for example, an aqueous high fructose corn syrup solution, or from an aqueous solution of one or more of the alcohols of such pentoses and hexoses, for example, from an aqueous sorbitol solution, by an acid-catalyzed dehydration using substituted sulfonic acids solubilized in the aqueous sugars or sugar alcohols solution.

19 Claims, 10 Drawing Sheets

PROCESSES FOR MAKING SUGAR AND/OR SUGAR ALCOHOL DEHYDRATION PRODUCTS

BACKGROUND

The present invention is concerned with processes for making dehydration products from sugars and/or from sugar alcohols, and more particularly but without limitation, to acid-catalyzed processes for making such dehydration products as hydroxymethylfurfural (HMF), levulinic acid and furfural from the pentose and/or hexose sugars and for making isohexides, such as isosorbide, from hexitols such as sorbitol.

Those skilled in the art have long appreciated that agricultural raw materials provide an inexpensive and renewable source of carbohydrates that could in turn be made into a variety of useful materials which are now made or derived from non-renewable feedstocks or into other, biobased or renewable source-derived materials that may have similar properties and utilities. Certain of these other, biobased or renewable source-derived materials have been conceived or proposed (as further elaborated below) based upon the dehydration products that can be made from, e.g., the pentose and hexose sugars or sugar alcohols such as sorbital which may be obtained by hydrogenating dextrose.

For its part, the particular sugar dehydration product HMF and its related 2,5-disubstituted furanic derivatives are of interest for a variety of applications and uses. More particularly, due to its various functionalities, it has been proposed that HMF could be utilized to produce a wide range of products such as polymers, solvents, surfactants, pharmaceuticals, and plant protection agents, and HMF has been reported to have antibacterial and anticorrosive properties. HMF is also a key component, as either a starting material or intermediate, in the synthesis of a wide variety of compounds, such as furfuryl alcohols, aldehydes, esters, ethers, halides and carboxylic acids.

In addition, HMF has been considered as useful for the development of biofuels, fuels derived from biomass as a sustainable alternative to fossil fuels. HMF has additionally been evaluated as a treatment for sickle cell anemia. In short, HMF is an important chemical compound and a method of synthesis on a large scale to produce HMF absent significant amounts of impurities, side products and remaining starting material has been sought for nearly a century.

Unfortunately, while it has long been known that HMF could be prepared from readily obtainable hexose carbohydrates, for example by acid-catalyzed dehydration methods, a method which provides HMF economically, with good selectivity and in high yields, has yet to be found. Complications for selectivity and yield arise from the rehydration of HMF, which yields by-products, such as, levulinic and formic acids. Another unwanted side reaction includes the polymerization of HMF and/or fructose resulting in humin polymers, which are solid waste products. Further complications may arise as a result of solvent selection. Water is easy to dispose of and dissolves fructose, but unfortunately, low selectivity and increased formation of polymers and humin increases under aqueous conditions. The purification of HMF has also proved to be a troublesome operation. On long exposure to temperatures at which the desired product can be distilled, HMF and impurities associated with the synthetic mixture tend to form tarry degradation products. Because of this heat instability, a falling film vacuum still must be used. Even in such an apparatus, resinous solids form on the heating surface causing a stalling in the rotor and frequent shut down time making the operation inefficient. Prior work has been performed with distillation and the addition of a non-volatile solvent like PEG-600 to prevent the buildup of solid humin polymers (Cope, U.S. Pat. No. 2,917,520). Unfortunately, the use of polyglycols leads to the formation of HMF-PEG ethers.

As to another sugars dehydration product, namely, levulinic acid, the National Renewable Energy Laboratory (Denver, USA) has identified levulinic acid as one of a number of key sugar-derived platform chemicals that can be produced from biomass. Levulinic acid can be used to produce a variety of materials for a variety of uses, including succinic acid, 1,4-butanediol, 1,4-pentanediol, tetrahydrofuran, gamma valerolactone, ethyl levulinate and 2-methyl-tetrahydrofuran, for example, for producing resins, polymers, herbicides, pharmaceuticals and flavoring agents, solvents, plasticizers, antifreeze agents and biofuels/oxygenated fuel additives.

Rackemann and Doherty, "The Conversion of Lignocellulosics to Levulinic Acid", Biofuels, Bioproducts & Biorefining, 5:198-214 (2011) provide an overview of current and potential technologies which had been publicly identified or suggested, for producing levulinic acid from lignocellulosics. The "most promising" commercial process according to the reviewers utilized the Biofine™ technology developed by Fitzpatrick (and described for example in U.S. Pat. No. 5,608, 105), involving a two-stage acid-catalyzed process wherein in a first, plug flow reactor a carbohydrate-containing material (primary sludges from paper manufacture, waste paper, waste wood, agricultural residues such as corn husks, corn cobs, rice hulls, straw, bagasse, food processing wastes from corn, wheat oats and barley) is dehydrated to 2,5-hydroxymethylfurfural (HMF) at from 210 to 230 degrees Celsius for less than 30 seconds, and then levulinic acid is produced in a second reactor at 195 to 215 degrees Celsius for 15 to 30 minutes. The reviewers conclude that further improvements must be made, however, for the cost-effective production of levulinic acid from biomass, in particular citing yield losses from re-polymerization and side reactions.

The Rackemann and Doherty review (at page 203) further recognizes that levulinic acid may also be obtained from furfural, another sugars dehydration product—from pentoses in the hemicellulosic fraction of biomass—by catalytically reducing the furfural through the addition of hydrogen to form furfuryl alcohol, and then converting the furfuryl alcohol to levulinic acid and alkyl levulinates. Similarly, in U.S. Pat. No. 7,265,239 to Van De Graaf et al, furfuryl alcohol and water are converted to levulinic acid with the use of a porous strong acid ion-exchange resin, or furfuryl alcohol with an alkyl alcohol are converted to an alkyl levulinate. Still earlier references describe other means for converting the pentoses in the hemicellulosic fraction of biomass into levulinic acid and/or its derivatives, by means of furfural and furfuryl alcohol, see, for example, U.S. Pat. Nos. 2,738,367; 4,236,012; 5,175,358; 2,763,665; 3,203,964; and 3,752,849.

The dehydration products that can be made by the acid-catalyzed dehydration of sugar alcohols, in particular, hexitols such as sorbitol, have also been the subject of extensive work. Isosorbide, also known as 1,4,3,6-dianhydrosorbitol, is now commercially produced and marketed as a monomer for imparting renewable content to polyesters and polycarbonates, and has been used as a pharmaceutical intermediate.

A variety of acid catalysts have been evaluated for use in carrying out the dehydration of carbohydrates or of alcohols based on such carbohydrates in order to provide the corresponding dehydration products, such as the above-mentioned HMF, levulinic acid, furfural and isosorbide. Inorganic acids such as $H_2SO_4$, $H_3PO_4$, and HCl are readily obtained, inexpensive materials but are difficult to regenerate. In order to avoid the regeneration and attendant disposal problems, solid resin catalysts have been tried. Unfortunately, in the presence of water and at the temperatures required for carrying out the dehydration, very few solid acids can demonstrate the activity and stability needed to begin to contemplate a commercially viable process.

WO 20091012445 by Dignan et al. is an example of a proposed process for making HMF using the inorganic acids. In Dignan, HMF is proposed to be made by mixing or agitating an aqueous solution of fructose and inorganic acid catalyst with a water immiscible organic solvent to form an emulsion of the aqueous and organic phases, then heating the emulsion in a flow-through reactor at elevated pressures and allowing the aqueous and organic phases to phase separate. HMF is present in the aqueous and organic phases in about equal amounts, and is removed from both, for example, by vacuum evaporation and vacuum distillation from the organic phase and by passing the aqueous phase through an ion-exchange resin. Residual fructose stays with the aqueous phase. High fructose levels are advocated for the initial aqueous phase, to use relatively smaller amounts of solvent in relation to the amount of fructose reacted.

WO 2009/076627 by Sanborn et al. is an example of a proposed process utilizing solid acid resins. In Sanborn '627, substantially pure HMF, HMF esters or HMF ethers are said to be provided from a carbohydrate source by contacting the carbohydrate source with a solid phase catalyst; "substantially pure" was defined as referencing a purity of HMF of about 70% or greater, optionally about 80% or greater, or about 90% or greater. In one embodiment, a carbohydrate starting material is heated with a solvent in a column, and the heated carbohydrate and solvent are continuously flowed through a solid phase catalyst in the presence of an alcohol to form a HMF ether. The solvent is removed by rotary evaporation to provide a substantially pure HMF ether. In another embodiment, a carbohydrate is heated with an organic acid and a solid catalyst in a solution to form an HMF ester. The resulting HMF ester may then be purified by filtration, evaporation, extraction, and distillation or any combination thereof.

U.S. Pat. Nos. 6,849,748; 7,420,067; 7,439,352; 7,772,412 and 7,982,059 provide examples of prior art methods for producing isohexides (also referred to as anhydrosugar alcohols, anhydrohexitols, anhydroalditols etc) such as isosorbide, from sorbitol from dextrose. Commonly-assigned U.S. Pat. No. 6,849,748 to Moore et al., for example, describes a solvent-free process wherein a sugar alcohol—such as sorbitol—is heated with stirring until molten, and then dehydrated in the presence of a soluble acid or acidic ion exchange resin with stirring, under vacuum (to remove the water product and drive the reaction toward the products) and at all elevated temperature, then the resulting anhydrosugar alcohol is purified by distillation, followed by melt crystallization and/or redistillation. The final, purified product is isolated by centrifugation or filtration. Enumerated preferred acid catalysts include sulfuric acid, phosphoric acid, p-toluenesulfonic acid, and p-methanesulfonic acid. Commonly-assigned U.S. Pat. No. 7,420,067 mentions these same acids, as well as acidic ion exchange resins and acidic zeolite powders as additional options. Successive film evaporators, especially wiped film evaporators under vacuum, are described for use in purifying the product isosorbide.

More recently, U.S. Pat. No. 7,772,412 to Holladay et al. describes a process for making isosorbide wherein sorbitol is fed to a reactor containing a dehydration catalyst and a hydrogenation co-catalyst, with hydrogen being supplied countercurrently to the reactor for removing water as it is formed and for "reducing or eliminating . . . oligomeric or polymeric material in the dehydration product", to which undesirable color formation had been attributed. Suitable dehydration catalysts include the mineral acid catalysts, solid acid catalysts such as the heteropolyacids, mesoporous silicas, acid clays, sulfated zirconia, molecular sieve materials, cation exchange resins and zeolites, and combinations of any of these. The hydrogenation catalyst is described as typically being a supported metal or multi-metal catalyst. Palladium in particular is described as especially preferable for the metal, with platinum, nickel, cobalt, ruthenium, rhenium, rhodium, iridium and iron also being listed.

Still more recently, U.S. Pat. No. 7,982,059 describes a process for converting aqueous sorbitol to xylitol and isosorbide in the presence of an acid catalyst and without a hydrogenation co-catalyst, more particularly involving reacting an aqueous sorbitol solution with an acid zeolite at about 250 degrees Celsius and a pressure maintained at from about 68 bars to about 80 bars to produce the xylitol and isosorbide.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this in mind, the present invention relates in one aspect to a process for making one or more dehydration products from an aqueous sugars solution including one or more of the pentoses and hexoses, wherein the aqueous sugars solution is subjected to an acid-catalyzed dehydration using a substituted sulfonic acid catalyst solubilized in the aqueous sugars solution. In certain embodiments, a product mixture results including the one or more dehydration products and further including residual sugars. For these embodiments, the product mixture is then preferably further processed to substantially remove the substituted sulfonic acid catalyst and to substantially separate the one or more dehydration products from the residual sugars, so that the residual sugars can be put to further productive use as indicated hereafter.

In another aspect, derivatives of the dehydration products from the pentoses and/or hexoses in the aqueous sugars solution, for example, ether derivatives of the hexose dehydration product hydroxymethylfurfural (HMF) as generally described in WO 20061063220 to Sanborn, can be made through the addition of a further reactant with the aqueous sugars solution; for the formation of HMF ethers via the dehydration of an aqueous sugars solution including one or more hexoses, the further reactant comprises an alcohol, while for the formation of HMF esters the further reactant preferably comprises an organic acid (for example, a carboxylic acid such as acetic acid).

In certain embodiments involving the preparation of the dehydration products of sugars or of the derivatives thereof as just mentioned, an aqueous sugars solution is dehydrated which comprises one or both of glucose and fructose (more preferably being comprised of both, in the common ratios associated with commercial high fructose corn syrup products), and the acid-catalyzed dehydration step is conducted rapidly and with rapid cooling of the dehydration products// unconverted sugar mixture prior to any separation of the residual sugars from the dehydration products in the overall product mixture, as described in copending, commonly assigned International Patent Application No. PCT/US2012/066708, filed Nov. 28, 2012 for "Process For Making HMF And HMF Derivatives From Sugars, With Recovery Of Unreacted Sugars Suitable For Direct Fermentation To Ethanol" (the "WO '708 application" or "WO '708"), such application being incorporated herein by reference in its entirety.

With respect to a process conducted as described in the incorporated application, by accepting limited per-pass conversion to HMF, the overall exposure of the HMF that is formed from any given aqueous hexose solution to acidic, elevated temperature conditions is limited, and preferably little to no unwanted or unusable byproducts such as humins are produced requiring waste treatments. Separation and recovery of the products is simplified and levels of HMF and other hexose dehydration products known to inhibit ethanol production by fermentation are reduced in the residual sugars product to an extent whereby the residual sugars product are suitable for being supplied directly to a fermentation process for producing ethanol, or for use in fermentations to produce lysine or lactic acid, for making levulinic acid (for example, according to a process described in a copending, commonly assigned US patent application referenced below), for making sugar alcohols and derivative products therefrom, for making additional HMF and/or HMF derivatives by recycling the unconverted sugars to the beginning of the dehydration process, and so forth and so on. We have found, further, that processes conducted as described in the incorporated application (and as described more summarily below) can be characterized by very high sugar accountabilities and high conversion efficiencies, with very low losses of sugars being apparent.

Moreover, with respect to a process of the present invention according to the more general, first aspect summarized above, we have discovered that certain substituted sulfonic acid materials—not previously known or suggested for such uses—may be satisfactorily used in the presence of water and at the temperatures involved in carrying out the dehydration, while being concurrently capable of being solubilized in the aqueous sugars solution in catalytically effective amounts at dehydration or near dehydration conditions and also readily separable from the resultant product mixture at the conclusion of the dehydration process, so that the substituted sulfonic acid catalysts may be recovered for reuse as part of a process for recovering a usable residual sugars product on the one hand, and the one or more dehydration products on the other. In this regard, as will be evident to those skilled in the art from the more detailed description following, various methods for combinations of methods) may be used for separating and recovering a usable residual sugars product from the one or more dehydration products, or for separating the sulfonic acid catalyst materials from either or both of the residual sugars product and the one or more dehydration products, or for mutually separating all of these from one another, for example, using solvent extraction, chromatographic methods and/or adsorption/desorption methods.

In another aspect, the present invention relates to a process for forming one or more dehydration products from an aqueous sugar alcohols solution including one or more alcohols from pentoses and hexoses, wherein the aqueous sugar alcohols solution is subjected to an acid-catalyzed dehydration using a substituted sulfonic acid catalyst solubilized in the aqueous sugar alcohols solution.

In still another aspect, the present invention relates to a process for forming ester and ether derivatives of the dehydration products of the sugar alcohols, by including a further organic acid or alcohol reactant with the aqueous sugar alcohols solution and subjecting dehydration products of the sugar alcohols to an acid-catalyzed esterification or etherification to the ester or ether derivatives, in the presence of a substituted sulfonic acid catalyst solubilized in the aqueous sugar alcohols solution.

In still another aspect, the dehydration process for forming the sugar alcohol dehydration products or for forming derivatives of these is conducted rapidly and with rapid cooling of the dehydration products (or dehydration product derivatives)//unconverted sugar alcohol mixture prior to any separation of the residual sugar alcohol(s) from the dehydration products/dehydration product derivatives in the overall product mixture, in the same manner as described in the WO '708 application for the dehydration of aqueous sugar solutions.

DETAILED DESCRIPTION OF PREFERRED EMBODIMENTS

Figure 1:
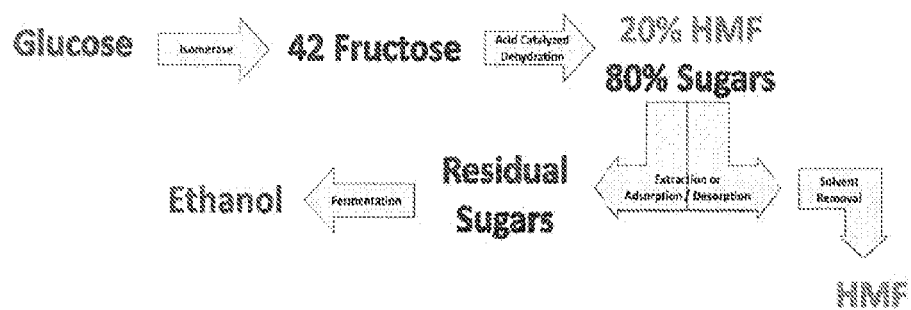
FIG. 1 is a schematic representation of a process of the incorporated application in a preferred embodiment, in which the just-referenced sulfonic acid materials may be employed.

As briefly summarized above, the present invention relates in a first aspect to a process for making one or more dehydration products from an aqueous sugars solution including one or more of the pentoses and hexoses, through the use of substituted sulfonic acid catalysts solubilized in the aqueous sugars solution in question.

An aqueous sugars solution of the type described can arise in various contexts. For example, the use of biomass—of materials whose carbon content is of biological rather than fossil origin—for providing chemicals and fuel products presently derived from fossil-origin materials such as petroleum, or for providing acceptable biobased, functional alternatives to such chemicals and fuel products, has increasingly become a focus of research and development investment and effort in recent years as supplies of fossil-origin materials have been compromised or been more difficult or expensive to acquire and use.

Lignocellulosic biomasses (such as grasses, sweet sorghum, fast growing trees, wood wastes (such as prunings, wood chips, sawdust) and green wastes (for instance, leaves, grass clippings, vegetable and fruit wastes)) are comprised mainly of cellulose, hemicellulose and lignin fractions, with cellulose being the largest of these three components. Cellulose derives from the structural tissue of plants, and consists of long chains of beta glucosidic residues linked through the 1,4 positions. These linkages cause the cellulose to have a high crystallinity. Hemicellulose by contrast is an amorphous heteropolymer, while lignin is an aromatic three-dimensional polymer interspersed among the cellulose and hemicellulose within a plant fiber cell.

Because of the differences in the cellulosic, hemicellulosic and lignin fractions of biomass, as well as considering other lesser fractions present in various biomasses to different degrees, as related in U.S. Pat. No. 5,562,777 to Farone et al., "Method of Producing Sugars Using Strong Acid Hydrolysis of Cellulosic and Hemicellulosic Materials", a number of processes have been developed or proposed over the years to fractionate lignocellulosic biomasses. Most involve hydrolyzing the cellulosic and hemicellulosic fractions into C6 and C5 sugars.

Fundamentally both biological and non-biological processes have been disclosed, with the oldest and best known non-biological methods of producing sugars from cellulose involving acid hydrolysis, most commonly sulfuric acid-based hydrolysis using a dilute acid approach, a concentrated acid approach or a combination of the two. The '777 patent to Farone et al. describes the advantages and disadvantages of the various sulfuric acid-based processes then known to the art, and suggests a further variation using strong acid/sulfuric acid hydrolysis and employing one or more iterations of a combination of a decrystallization step wherein the biomass (and/or including the solids left from the decrystallization step in a previous iteration) is mixed with a 25-90 percent sulfuric acid solution to solubilize a portion of the biomass, then the acid is diluted to between 20 and 30 percent and the mixture heated to preferably between 80 and 100 degrees Celsius for a time to solubilize the cellulosic fraction and any hemicellulosic material that had not been hydrolyzed.

Commonly-assigned WO2011/097065, for "Methods for Producing Sugars Using a Combination of Acids to Selectively Hydrolyze Hemicellulosic and Cellulosic Materials", and WO2011/097075, for "Improved Process for Fractionation of Lignocellulosic Biomass", describe additional methods by which aqueous sugars solutions including pentoses, hexoses or both can be generated by acid hydrolysis from lignocellulosic biamasses, and are incorporated by reference herein.

An aqueous sugars solution of the type described can arise in another important context, wherein the aqueous sugars solution is an aqueous hexose sugars solution, and especially is an aqueous hexose sugars solution including both of glucose and fructose (aqueous hexose sugars solutions of this character being routinely produced in certain glucose/fructose combinations in the form of high fructose corn syrups (HFCS), or being susceptible of being readily made using existing HFCS manufacturing infrastructure). In this second industrially-important context, a process is contemplated for making HMF and/or levulinic acid from the aqueous hexose sugars solution, wherein the aqueous hexose sugars solution is subjected to an acid-catalyzed dehydration using a substituted sulfonic acid catalyst solubilized in the aqueous hexose sugars solution, to produce a product mixture including one or more dehydration products inclusive of one or both of HMF and levulinic acid and, in certain embodiments, further including residual sugars. The product mixture is then preferably further processed to substantially remove the substituted sulfonic acid catalyst and to substantially separate the one or more dehydration products from the residual sugars.

We have beneficially discovered in regard to the use of such substituted sulfonic acid catalysts, rather than the inexpensive inorganic acids (that as mentioned have proven difficult to regenerate from the dehydration product mixture) or the solid, sulfonic acid catalysts that have been suggested and evaluated as a further alternative to sulfuric acid and other inorganic acids, that certain substituted sulfonic acid materials—not previously known or suggested for such uses—may be satisfactorily used in the presence of water and at the temperatures involved in carrying out the dehydration, while being concurrently capable of being solubilized in the aqueous sugars solution in catalytically effective amounts at dehydration or near-dehydration conditions and also readily separable from the resultant product mixture at the conclusion of the dehydration process, so that the substituted sulfonic acid catalysts may be recovered for reuse as part of a process for recovering a usable residual sugars product on the one hand, and the one or more dehydration products on the other.

Suitable substituted sulfonic acids may include: dinonylnaphthalene sulfonic acid (DNSA, CAS No. 25322-17-2, solubility reported as $2.8 \times 10^{-5}$ mg/liter); 6-amino-m-toluenesulfonic acid (CAS No. 88-44-8, also known as 2-amino-5-methylbenzene sulfonic acid, reported solubility of 0.47% on the basis of the total mass of solute and solvent): linear alkylbenzene sulfonic acid (such as Calsoft® LAS-99 linear alkylbenzene sulfonic acid, comprising minimum 97% of C10-C16 alkyl derivatives of benzenesulfonic acid, reported solubility of "up to 10% with difficulty" by its manufacturer); branched dodecylbenzene sulfonic acid (such as Calimulse® EM-99 branched dodecylbenzene sulfonic acid, comprising min. 97% branched dodecylbenzene sulfonic acid, CAS No. 68411-32-5, reported solubility less than that of Calsoft® LAS-99 linear alkylbenzene sulfonic acid); Calsoft® LPS-99 linear alkylbenzene sulfonic acid, comprising from 97 to 99% of C10-C16 alkyl derivatives of benzenesulfonic acid (CAS No. 68584-22-5) and 0.5 to 1.0 percent of C10-C16 alkyl benzene derivatives, reported solubility between Calsoft® LAS-99 and Calimulse® EM-99 materials; or Aristonic® acid (alkylarylsulfonic acid, Pilot Chemical, especially as sold under grades 9800 and 9900, having reported solubilities "well less than 1 percent").

Other substituted sulfonic acids may be used as well, provided any sulfonic acid selected for use can be characterized as both a) capable of solubilization in catalytically effective amounts in the aqueous sugars solutions under dehydration or near-dehydration conditions (for example, after a not overly-long period of cooling down of the product mixture) and b) capable of substantially separating out of the product mixture through formation of a salt or of being substantially extracted into a solvent that the dehydration product(s) will not extract into, or of substantially separating out of the product mixture in a filterable mass with further cooling and/or with removal of additional water from the final product mixture. Preferred substituted sulfonic acids will generally be characterized by a solubility of not more than about 10%, in keeping with the "most soluble" of the specific named substituted sulfonic acids above.

All of the specified substituted sulfonic acids are commercially available from various sources, and are characterized by low volatilities and vapor pressures, high viscosities and low solubility in water. These materials have typically been used as additives in industrial lubricants, greases, metalworking fluids, industrial coatings, household and industrial cleaners, and rust preventatives. Several are indicated to be biodegradable by their manufacturer in relation to their long chain-substituted, hydrophobic character, and these may be generally preferred considering contemplated uses of the dehydration products and of the residual sugars from the product mixture.

Somewhat unexpectedly, it was observed (as shown in the examples below and the accompanying Figures) that differently-substituted sulfonic acids performed differently in catalyzing the dehydration of an aqueous hexose sugar solution, though providing generally equivalent acid strengths (as indicated by the solution pH). More particularly, in relation to the specified substituted sulfonic acids, better conversion to HMF and better overall sugar accountabilities were indicated with the Calsoft® LAS-99, Calimulse® EM-99, Aristonic® acid and 6-amino-m-toluenesulfonic acid materials, while the Calimulse® EM-99 product appeared to perform better where the desired dehydration product was levulinic acid.

Catalyst loading should be such that the catalyst is substantially solubilized in the aqueous sugars solution (or in the combination of an aqueous sugars solution and other co-solvents which may be present, for example, an alcohol as employed to produce an HMF ether derivative product), under dehydration reaction conditions and until the catalyst is to be substantially removed.

Substantial removal of the substituted sulfonic acid catalysts and a substantial separation of the one or more dehydration products from residual sugars may be accomplished by various means, including, for example, one or more of solvent extraction, adsorption and desorption, and precipitation, for example, through forming derivatives of the sulfonic acids that are substantially insoluble in the aqueous hexose sugar solutions and/or in the sugar solutions and alcohols present at dehydration reaction or near-dehydration reaction temperatures, or through concentrating the product mixture and/or cooling so that the sulfonic acids separate out directly and can be recovered by conventional solid/liquid separation methods.

LEWATIT® AF-5 resin (LANXESS AG, Leverkusen, Germany), described by its manufacturer as a "carbon-based, spherical, microporous adsorber with a large surface area and a well-defined pore distribution", is an example of an adsorptive material which can be used to selectively adsorb the dehydration product HMF from the substituted sulfonic acid catalyst and residual sugars (with acetone having been found suitable for desorbing the HMF for further use, in the applications mentioned in the Background section); the substituted sulfonic acid catalyst can thereafter be substantially removed or separated from the residual sugars by selective adsorption of one or the other by a different material, by solvent extraction or by causing the sulfonic acid catalyst to substantially separate out in solid form as just discussed, whereupon the residual sugars can be forwarded for further use in other processes (as elaborated below) or recycled for reuse in making additional dehydration products.

Alternatively, of course, the substituted sulfonic acid catalysts can be substantially removed first, and the dehydration product or products and residual sugars can be separated through drawing upon the body of knowledge that has developed for this separation in past acid dehydration process work, see, for example, the commonly-assigned and copending WO '708 application, earlier incorporated by reference. Conventionally, solvent extraction with organic solvents has been favored for substantially separating HMF (and HMF derivatives) in an organic phase, while residual sugars are retained in an aqueous phase.

Substantial removal of the substituted sulfonic acid catalysts can again be by adsorption, solvent extraction or by separation in a filterable mass, with the latter being the preferred means. Extractions with ethyl acetate, methyl tert-butylether (MTBE), diethyl ether, methyl tetrahydrofuran (MTHF) and hexane were tried with at least one of the specified substituted sulfonic acids and were somewhat effective; further routine optimization can be expected to improve the degree of separation through solvent extraction, though generating a filterable mass (for example, through the formation of insoluble derivatives) and filtering are presently preferable.

Where the sulfonic acid catalyst is removed by generating a filterable mass and then filtering, for example by formation and filtering of an insoluble derivative as just mentioned, preferably the sulfonic acid catalyst will be regenerated for reuse. One method for accomplishing the regeneration from an insoluble derivative would include exposure to sulfuric acid.

A preferred embodiment 10 of a process as described in the copending, commonly assigned WO '708 application (such having been incorporated by reference herein) is shown schematically in FIG. 1, for describing a particular dehydration process in which the substituted sulfonic acid catalysts of the present invention can be used. Generally, the aqueous hexose solution used can comprise one or more of the six-carbon sugars (hexoses). In particular embodiments, the aqueous hexose solution can comprise one or both of the more common hexoses glucose and fructose and in certain preferred embodiments will comprise both of glucose and fructose. The embodiment 10 schematically shown in FIG. 1 is based on an aqueous hexose solution including both of glucose and fructose.

In the process 10, glucose as may be derived from the hydrolysis of starch with acids or enzymes or from the hydrolysis of cellulosic materials is first enzymatically converted in step 12 through use of an isomerase to a mixture of glucose and fructose, in the form of aqueous hexose sugar solution 14. Processes for making glucose from starch and for converting a portion of the glucose to fructose are well known, for example, in the making of high fructose corn syrups. Alternatively, of course, fructose derived from cane sugar or sugar beets, rather than from an isomerization of glucose, may be combined with glucose in a desired proportion. In still another embodiment, a combination of isomerization of glucose plus blending in of fructose from other known sources may be employed, to provide a combination of glucose and fructose for forming an aqueous hexose sugar solution for further processing. Preferably and conveniently, the aqueous hexose sugar solution 14 can correspond to a current high fructose corn syrup product, for example, HFCS 42 (containing about 42 percent fructose and about 53 percent glucose), HFCS 90 (made from HFCS 42 by additional purification, about 90 percent fructose and about 5 percent each of glucose and maltose) or HFCS 55 (containing about 55 percent fructose, conventionally made from blending HFCS 42 and HFCS 90), so that existing HFCS production capacity can be utilized to make HMF and derivative products to improve asset utilization and improve returns on capital, as HFCS demand and pricing and HMF and HMF derivative demand and pricing would indicate.

The aqueous hexose sugar solution 14 then undergoes an acid dehydration in step 16, to provide a mixture 18 of HMF and unconverted sugars. Because fructose dehydrates much more readily than glucose, the proportion of glucose in the mixture 18 will be higher than in the hexose sugar solution 14. The relative amounts of HMF and of the unconverted hexose sugars in the mixture 18, and the relative amounts of glucose and fructose in the unconverted sugars portion, can vary dependent on the manner in which the acid dehydration step 16 is conducted as well as on the composition of the aqueous hexose sugar solution 14. In general, of course, where HMF production is to be favored over the production of ethanol from the unconverted, residual sugars. HFCS 90 will produce more HMF given the same acid dehydration conditions than will HFCS 55, and HFCS 55 will produce more than HFCS 42.

In preferred embodiments, the acid-catalyzed dehydration step 16 is conducted rapidly and with rapid cooling of the HMF/unconverted sugar mixture 18 prior to the separation of the fermentation-ready residual sugars product from the HMF product. By accepting limited per-pass conversion to HMF in this fashion, the overall exposure of the HMF that is formed to acidic, elevated temperature conditions is correspondingly limited, so that preferably little to no unwanted or unusable by products such as humins are produced requiring waste treatments. Separation and recovery of the products is simplified and levels of HMF and other hexose dehydration products known to inhibit fermentation, for example, to produce ethanol, are reduced in the residual sugars product to an extent whereby the residual sugars product can be used directly for this or for other purposes (e.g., in fermentations to produce lactic acid or lysine).

Consequently, typically the mixture 18 will comprise from about 10 to about 55 percent molar yield of HMF, from about 30 to about 80 percent molar yield of unconverted, residual sugars, and not more than about 10 percent molar yield of other materials such as furfural, levulinic acid, humins etc. Preferably, the mixture 18 will comprise from about 25 to about 55 percent yield of HMF, from about 40 to about 70 percent yield of unconverted, residual sugars, and not more than about 5 percent yield of other materials such as furfural, levulinic acid, humins etc. More preferably, the mixture 18 will comprise from about 30 to about 50 percent yield of HMF, from about 25 to about 50 percent yield of unconverted, residual sugars, and not more than about 5 percent yield of other materials such as furfural, levulinic acid, humins etc.

Returning now to FIG. 1, the HMF and unconverted, residual sugars in mixture 18 are then separated by adsorption, solvent extraction, or a combination of these in separation step 20, to yield an HMF product stream or portion 22 and a fermentation-ready sugars stream or portion 24 which can optionally be supplied to an ethanol fermentation step 26 for producing an ethanol product 28. It will be appreciated that this separation of the dehydration products and the residual sugars can be accomplished before, after or concurrently with the preferred recovery of the sulfonic acid catalyst, as desired, with a proper selection of the various separation methods that will be well within the capabilities of those skilled in the art.

Adsorption in step 20 can be by means of any material which preferentially adsorbs HMF from the residual hexose sugars in the mixture 18. A material which has been found to be very effective at retaining the HMF and the small amounts of levulinic acid formed is DOWEX® OPTIPORE® V-493 macroporous styrene-divinylbenzene resin (CAS 69011-14-9, The Dow Chemical Company, Midland, Mich.), which has been described by its manufacturer as having a 20-50 mesh particle size, a 46 angstrom mean pore size and 1.16 mL/g pore volume, a surface area of 1100 sq. meters/g and a bulk density of 680 g/liter. An ethanol wash was effective for desorbing most of the adsorbed HMF, and subsequent washing of the resin with acetone provided quantitative recovery of the HMF that was adsorbed. An alternative is AMBERLITE™ XADT™-4 polystyrene divinylbenzene polymeric adsorbent resin (CAS 37380-42-0, Rohm & Haas Company, Philadelphia, Pa.), a non-functionalized resin having a 1.08 g/mL dry density, a surface area of 725 square meters per gram, an average pore diameter of 50 angstroms, a wet mesh size of 20-60 and a pore volume of 0.98 mL/gram. Other suitable adsorbents can be activated carbon, zeolites, alumina, clays, non-functionalized resins (LEWATIT® AF-5, LEWATIT® S7968, LEWATIT® VPOC1064 resins, all from Lanxess AG and DIANION® SP850, from Mitsubishi Chemical), cation exchange resins, see U.S. Pat. No. 7,317, 116 B2 (Sanborn) and the later U.S. Pat. No. 7,897,794 (Geier and Soper).

Suitable solvents for solvent extraction include methyl ethyl ketone and especially ethyl acetate, due to the latter's great affinity for HMF and levulinic acid, low boiling point (77 deg. C.) and ease of separation from water. As demonstrated in certain of the examples below, virtually complete recovery of the sugars and of the HMF from mixture 18 was accomplished through a series of ethyl acetate extractions. Additionally, while the residual sugars recovered by other means were still suitable for being directly processed to ethanol in the subsequent ethanol fermentation step 26, those recovered following the quantitative extraction with ethyl acetate were observed to be significantly less inhibitory even under non-optimal conditions. A variety of other solvents have been suggested or used in the literature related to HMF and HMF derivative synthesis and recovery in biphasic systems, and these may be appropriate for use in the context of the present invention. Examples of other useful solvents are butanol, methyl ethyl ketone, methyl isobutyl ketone, diethyl ether, cyclopentyl dimethyl ether, methyl tetrahydrofuran, and methyl t-butyl ether.

Ethanol fermentation step 26 can encompass any known process whereby a hexose sugars feed of the type represented by fermentation-ready sugars stream or portion 24 may be converted to one or more products inclusive of ethanol, at least in some part by fermentation means. Both aerobic and anaerobic processes are thus contemplated, using any of the variety of yeasts (e.g., *kluyveromyces lactis kluyveromyces lipolytica, saccharomyces cerevistae, s. uvarurn, s. monacensis, s. pastorianus, s. bayanus, s. ellipsoidues, candida shehata, c. melibiosica, c. intermedia*) or any of the variety of bacteria (e.g., *clostridium sporogenes, c. indolts, c. sphenoides, c. sordelli, candida bracarensis, candida dubliniensis, zymomonas mobilis, z. pomaceas*) that have ethanol-producing capability from the fermentation-ready sugars stream or portion 24 under aerobic or anaerobic conditions and other appropriate conditions. The particular yeasts (or bacteria) used and other particulars of the fermentations employing these various yeasts (or bacteria) are a matter for routine selection by those skilled in the fermentation art, though the examples below demonstrate the functionality of one common anaerobic yeast strain, *saccharomyces cerevisiae*. Given that the sugars stream or portion 24 derives from a process for making the acid dehydration product HMF, a yeast or bacteria that has been demonstrated for use particularly with sugars derived from a lignocellulosic biomass through acid-hydrolyzing the biomass and/or a cellulosic fraction from biomass may be preferred. For example, the aerobic bacterium *corynebacterium glutamicum* R was evaluated in Sakai et al., "Effect of Lignocellulose-Derived Inhibitors on Growth of and Ethanol Production by Growth-Arrested *Corynebacterium glutamicum* R", Applied and Environmental Biology, vol. 73, no. 7, pp 2349-2353 (April 2007), as an alternative to detoxification measures against organic acids, furans and phenols byproducts from the dilute acid pretreatment of biomass, and found promising.

While the amounts of HMF (and/or HMF esters or ethers, as the case may be) and of unconverted, residual sugars may vary somewhat, preferably in all embodiments a high degree of sugar accountability is achieved, where "sugar accountability" is understood to refer to the percentage of sugars input to the acid dehydration step 16 that can be accounted for in adding the molar yields of identifiable products in the mixture 18 essentially adding the molar yields of HMF (and/or of HMF esters and ethers), levulinic acid and residual, unconverted sugars. Preferably, a process according to the present invention is characterized by a total sugar accountability of at least about 70 percent, more preferably at least about 80 percent and most preferably at least about 90 percent.

The fermentation-ready sugars stream or portion 24 can, in whole or in part, also be used for other purposes beyond the production of ethanol. For example, sugars in stream or portion 24 can be recycled to the beginning of the acid dehydration step 16 for producing additional HMF or HMF derivatives. The hexose sugars represented by stream or portion 24 can also be hydrogenated to sugar alcohols for producing other biobased fuels and fuel additives (other than or in addition to ethanol), see, for example, U.S. Pat. No. 7,678,950 to Yao et al. The sugars in stream or portion 24 can be fermented to produce lysine or lactic acid according to known methods, or used for making another dehydration product such as levulinic acid. Still other uses will be evident to those skilled in the art, given the character of the sugars stream or portion 24 provided by the described process.

A number of prospective uses of HMF product stream or portion 22 have already been mentioned, but one important contemplated use would be in the manufacture of 2,5-furandicarboxylic acid (FDCA) using a Mid-Century type Co/Mn/Br oxidation catalyst under oxidation conditions, as described in United States Pat. Application Publication No, US 2009/1056841 to Sanborn et al, and in copending International Application No. PCT/US2012/052641, filed Aug. 28, 2012 for "Process for Producing Both Biobased Succinic Acid and 2,5-Furandicarboxylic Acid", both of which are now incorporated herein by reference. Another contemplated use would be for making the more thermally-stable intermediate levulinic acid, particularly according to copending and commonly-assigned International Application No. PCT/US2012/066710, filed Nov. 28, 2012 for "Process for Making Levulinic Acid", which application is also incorporated by reference herein.

As previously indicated, the acid dehydration step 16 is preferably conducted in a manner to limit per-pass conversion to HMF and the exposure of the HMF that is formed to acidic, elevated temperature conditions. Rapid heating of the combined hexose sugar solution 14 and a selected substituted sulfonic acid catalyst, as well as rapid cooling of the HMF/unconverted sugar mixture produced from the acid dehydration step 16, are desirable for accomplishing these objectives. While optimal conditions will vary somewhat from one embodiment to the next, for example, in processing HFCS 42 versus HFCS 55 versus HFCS 90 as shown clearly below, in general terms for a catalyst loading of about 2% percent by weight of LAS-99 or Aristonic 9900 catalyst based on the mass of hexose sugars in the sugar solution 14, a reaction temperature of from about 175 degrees Celsius to about 190 degrees Celsius, a final dry solids loading of sugars in the range of from about 10 to about 20 percent, and an average residence or batch reaction time of from about 5 to about 17 minutes appear to be advantageous. "Average residence or reaction time" or similar terminology as used herein refers to the time elapsed from the introduction of the sugar solution 14 into a reactor until cooling of the mixture 18 is commenced.

As a general matter, of course, it would be preferable to process sugar solutions 14 having a greater loading of the hexose sugars rather than a lesser loading, though some trade-offs were observed in terms of overall sugars accountability and in other respects, and these would need to be considered in determining the optimum conditions to be observed for a given feedstock. Similarly, milder reaction conditions generally provide lesser conversion, but enable increased sugars accountability. Favored conditions for the recovered sugars in stream or portion 24, it should be noted, may differ from those contemplated for freshly-supplied sugars in sugar solution 14 where recycle is contemplated for making additional HMF product.

In any event, the heating to the desired reaction temperature is preferably accomplished in not more than about 17 minutes, preferably is accomplished in 10 minutes of less and more preferably in not more than about 8 minutes. Rapid cooling from the reaction temperature to about 50 degrees Celsius and lower is preferably accomplished in not more than about 5 minutes, especially 3 minutes or less.

It will be appreciated that the acid-catalyzed dehydration step 16 can be conducted in a batchwise, semi-batch or continuous mode. In a batch reactor (as clearly shown in the examples below) combining the sugar solution 14 and the acid catalyst in a hot reactor already close to or at the desired reaction temperature provides improved results as compared to where the sugar solution 14 and acid catalyst are added to a reactor and then heated gradually together to the desired reaction temperature.

In regard to continuous processes, one suitable means for rapidly heating the sugar solution 14 and the acid catalyst would be direct steam injection. A commercially-available, in-line direct steam injection device, the Hydro-Thermal Hydroheater™ from Hydro-Thermal Corporation, 400 Pilot Court, Waukesha, Wis., injects sonic velocity steam into a thin layer of a liquid (such as the sugar solution 14) flowing from an inlet pipe through a series of gaps. Steam flow is adjusted precisely through a variable area nozzle to an extent whereby outlet fluid temperatures are claimed to be controllable within 0.5 degrees Fahrenheit over a large liquid turn-down ratio. Turbulent mixing takes place in a specifically designed combining tube, with an adjustable degree of shear responsive to adjustments of the steam flow and the liquid flow through (or pressure drop across) the series of gaps. Devices of this general character are described in, for example, U.S. Pat. Nos. 5,622,655; 5,842,497; 6,082,712; and 7,152,851.

Rapid cooling of the mixture 18 can be accomplished by various means. For example, while a brazed plate heat exchanger was used in at least certain of the examples below prior to a pressure reduction, other types of exchangers could be used. Other options will be evident to those of routine skill in the art.

A process for making derivatives of the dehydration products of sugars, and particularly HMF ether and ester derivatives, can be conducted as described above for the dehydration products but with the addition of further reactants with the aqueous sugars solution to be dehydrated. For example, ether derivatives of HMF as previously described in commonly-assigned WO 20061063220 of the type R-oxymethyl-furfural ether, where R is alkyl, cycloalkyl, allyl or aryl, may be made by incorporating the corresponding alkyl, cycloalkyl, allyl or aryl alcohols. Similarly, ester derivatives of the type described in commonly-assigned WO 2009/076627 may be made by incorporating organic acids such as acetic acid or citric acid.

The present invention also contemplates processes for forming one or more dehydration products from an aqueous sugar alcohols solution including one or more alcohols from the pentose and hexose sugars, wherein the aqueous sugar alcohols solution is subjected to an acid-catalyzed dehydration using a substituted sulfonic acid catalyst solubilized in the aqueous sugar alcohols solution. In certain embodiments, these processes will be conducted rapidly and with rapid cooling of the product mixture as described above with respect to forming the dehydration product(s) from an aqueous sugars solution. In other embodiments, processes for forming dehydration product(s) from sugar alcohols using the substituted sulfonic acid catalysts of the present invention can be conducted in a like manner as described above for forming dehydration product(s) from sugars, including for example forming ester and ether derivatives of the dehydration products of the sugar alcohols.

Unconverted starting sugar alcohols, such as sorbitol, can be separated from the resultant dehydration product(s) in keeping with known methods for separating, e.g., sorbitans and isosorbide from sorbitol. The unconverted starting sugar alcohols can be recycled for making additional isosorbide, of course, or as mentioned previously in connection with possible uses of the unconverted sugars can be supplied as a feed for a process for producing other biobased fuels and fuel additives (other than or in addition to ethanol), see, for example, U.S. Pat. No. 7,678,950 to Yao et al. Various other downstream options for unconverted sorbitol, the singly dehydrated sorbitans and isosorbide will be evident to those skilled in the art, but the recitation of those options need not be undertaken herein.

Those skilled in the art will appreciate, finally, that in the use, separation and recovery of the substituted sulfonic acid catalysts of the present invention, combination with other useful features and combinations of features of known methods for making the dehydration products of sugars (such as HMF and levulinic acid from fructose, glucose or a combination of these) or for making derivatives of these dehydration products, and with features of known methods for making the dehydration products of sugar alcohols (such as isosorbide from sorbitol) or for making derivatives of these dehydration products should be possible and may be advantageous. Thus, for example, the dehydration processes may be desirably conducted in biphasic systems with organic solvents or under vacuum to enable the continuous removal of water and drive the dehydration forward toward the desired dehydration product(s). An exhaustive description of the manner in which the substituted sulfonic acid catalysts can be utilized in modification of such known methods need not be undertaken herein, as those skilled in the art will be well able to make use of the substituted sulfonic acid catalysts in the context of these prior methods based on the teachings above and the examples that follow hereafter.

The present invention is illustrated by the following examples:

Examples 1-4

Figure 2A:
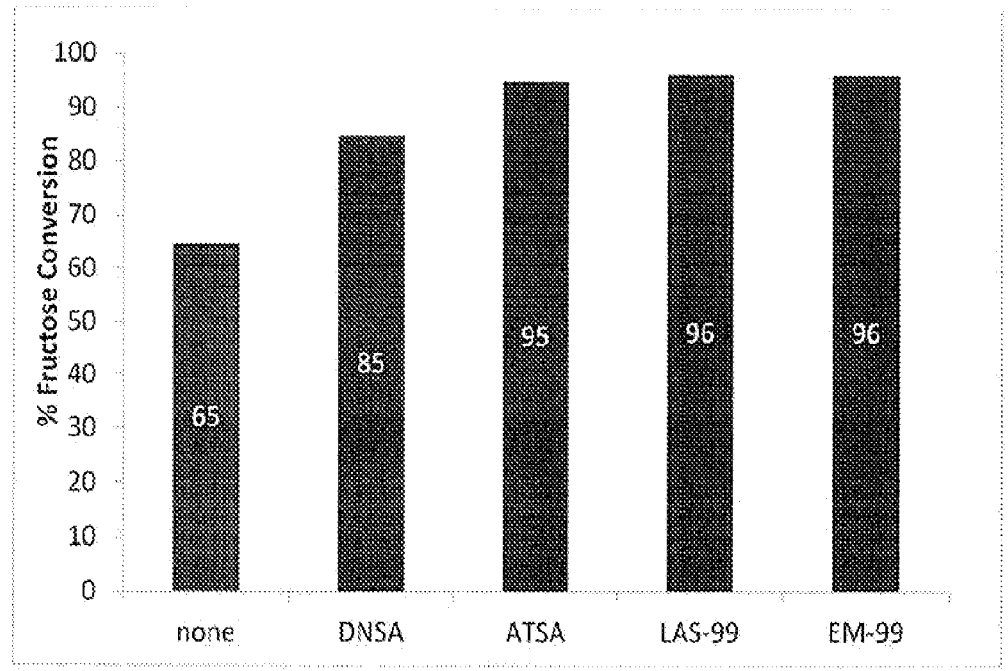
FIGS. 2A and 2B show the fructose conversion and molar yield percentages, respectively, from dehydrating a crystalline fructose solution using various substituted sulfonic acid materials as the acid catalyst.
Figure 2B:
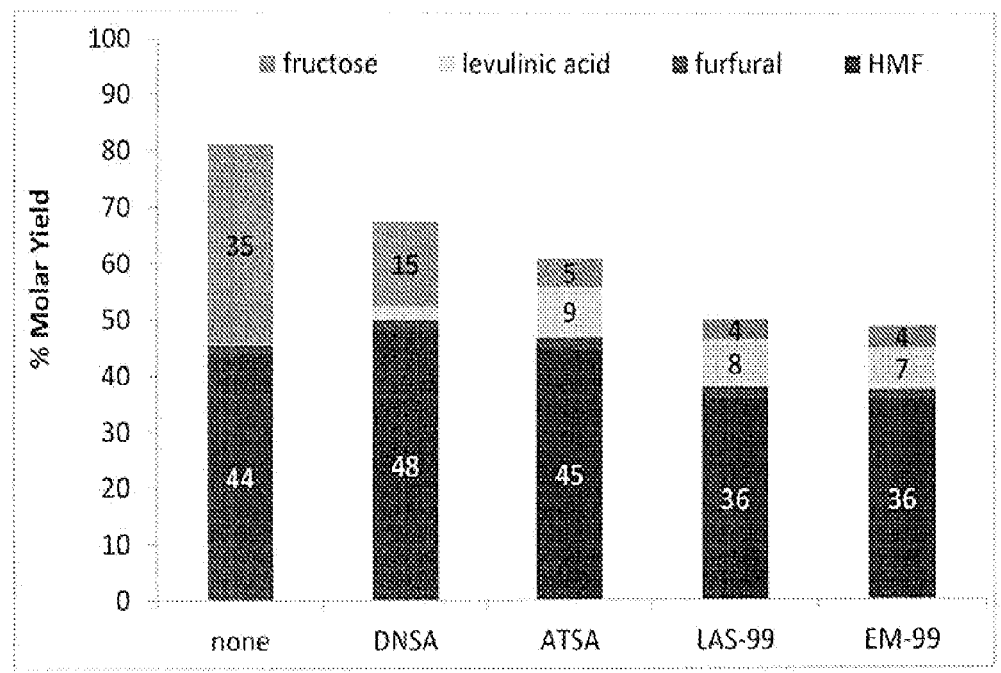

For Examples 1-4, an initial series of batchwise carbohydrate dehydration reactions was performed at a bench scale, using a Parr multireactor system (Parr Instrument Company, Moline, Ill.). For each run, a 75 mL reaction chamber was charged with a crystalline fructose sugar solution (5 percent by weight, on a dry solids basis) and with a selected substituted sulfonic acid catalyst at a loading of 2 percent based on total sugars. The reaction mixture was then heated to 180 degrees Celsius over a period of 25 min with magnetic stirring at a controlled rate of about 850 rpm. After reaching 180 degrees, the reaction was continued for 30 minutes at that temperature, then the product was rapidly cooled to about 30 degrees Celsius or less by submerging the vessel into an ice water bath. Analysis of the samples was by HPLC. The results are shown in FIGS. 2A and 2B for percentage fructose conversion and molar percentage yield of HMF, respectively, and demonstrate that the substituted sulfonic acids provide higher conversion of fructose, but comparable molar percentage yields and lower sugar accountability overall as compared to the "no catalyst" control.

Examples 5-9

Figure 3A:
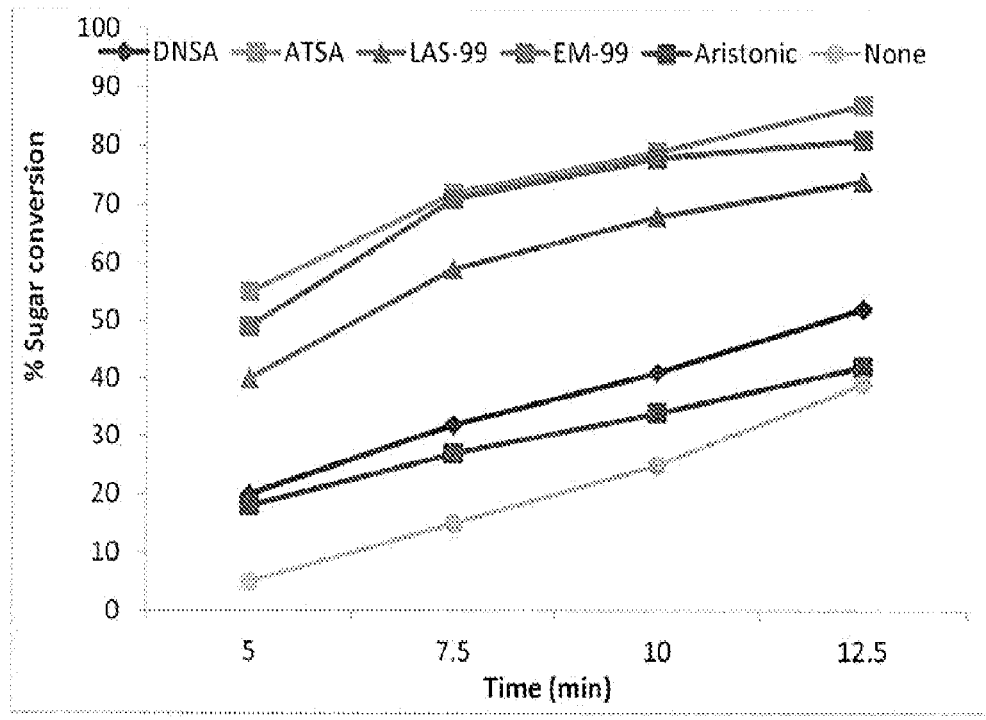
FIGS. 3A and 3B show the fructose conversion and HMF molar yield percentages, respectively, from using the same substituted sulfonic acid materials (plus another) for dehydrating a 20% solution of HFCS 90 in water, but with rapid heating of the sugar solution in keeping with the teachings of the WO '708 application.
Figure 3B:
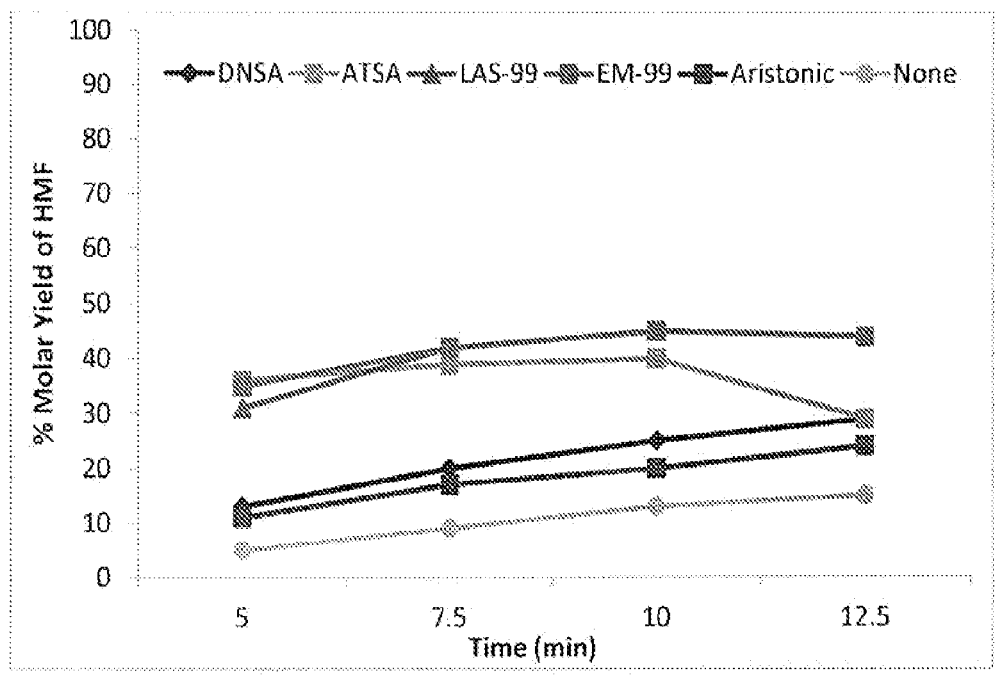
Figure 4A:
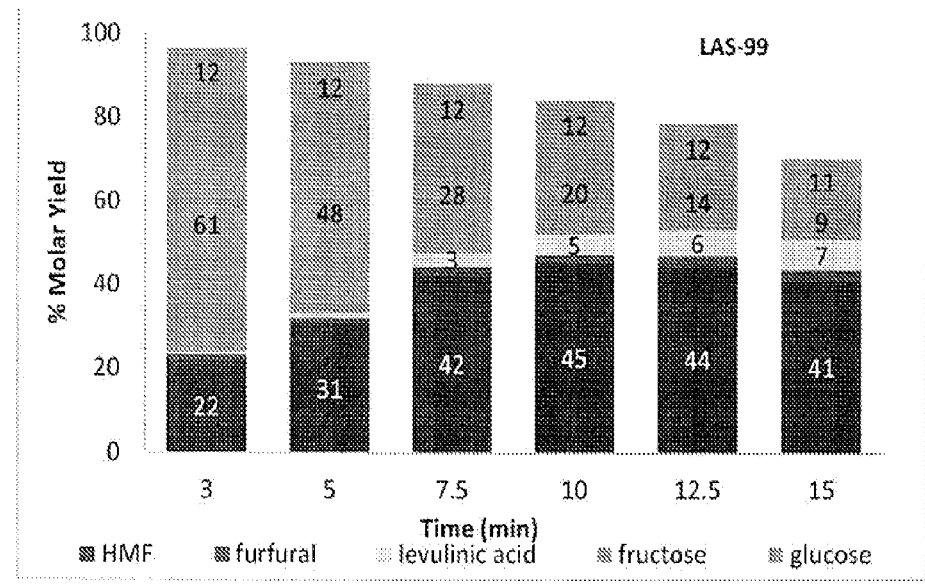
FIGS. 4A and 4B show the compositions of the products generated in connection with FIGS. 3A and 3B by using two of the substituted sulfonic acid materials shown, in experiments conducted at various reaction times.
Figure 4B:
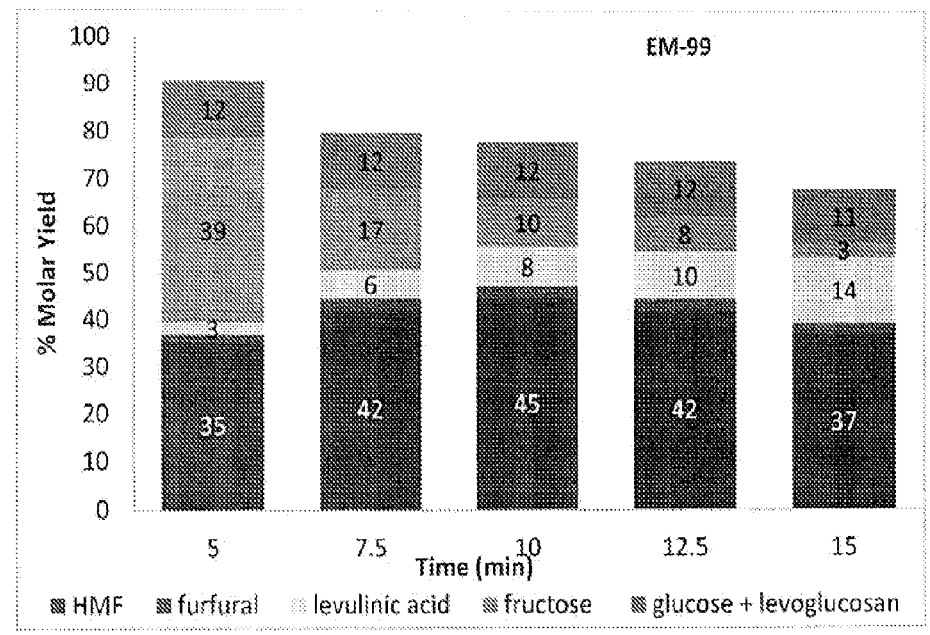

Using the same apparatus as used in Examples 1-4, a 75 mL reaction chamber was first charged with an acidic aqueous solution, containing a catalyst loading of 2 percent of a given one of the same substituted sulfonic acids as in Examples 1-4 or of an Aristonic® acid 9800 grade catalyst (in one instance, a "no catalyst" control was used, just as in Examples 1-4). The acidic aqueous solution was then heated to 180 degrees Celsius over a period of 25 min with magnetic stirring at a controlled rate of about 850 rpm. After this, an HFCS 90 sugar solution (at about 20 to about 25 percent hexoses by weight, on a dry solids basis) was rapidly introduced into the preheated acidic aqueous solution by an Eldex high pressure pump (Eldex Laboratories, Inc, Napa, Calif.) over a period of about 120 sec. The reaction was continued for the various, much shorter reaction times indicated in FIGS. 3A and 3B, then the product was flowed through a cooling coil consisting of ⅛" stainless steel tubing and into a collection vial. Analysis of the samples was by HPLC. The results are shown in FIGS. 3A and 3B for percentage fructose conversion and molar percentage yield of HMF, respectively. Yield for the "no catalyst" control in these rapid feeding/heating runs was at most only 18% on a molar yield percentage basis, at a reaction time of 12½ minutes. More detailed compositional analysis was conducted of the dehydration product mixtures that resulted at various reaction times with the two highest HMF-yielding catalysts (Calsoft® LAS-99 linear alkylbenzene sulfonic acid (FIG. 4A) and Calimulse® EM-99 branched dodecylbenzene sulfonic acid (FIG. 4B)), and these results are shown in FIGS. 4A and 4B. The LAS-99 catalyst gave about 10 percent less sugar conversion as compared to the EM-99 catalyst, but higher overall sugar accountability. The yield of levulinic acid was higher for the EM-99 catalyst, and no significant glucose conversion was found in either case.

Example 10

Figure 5A:
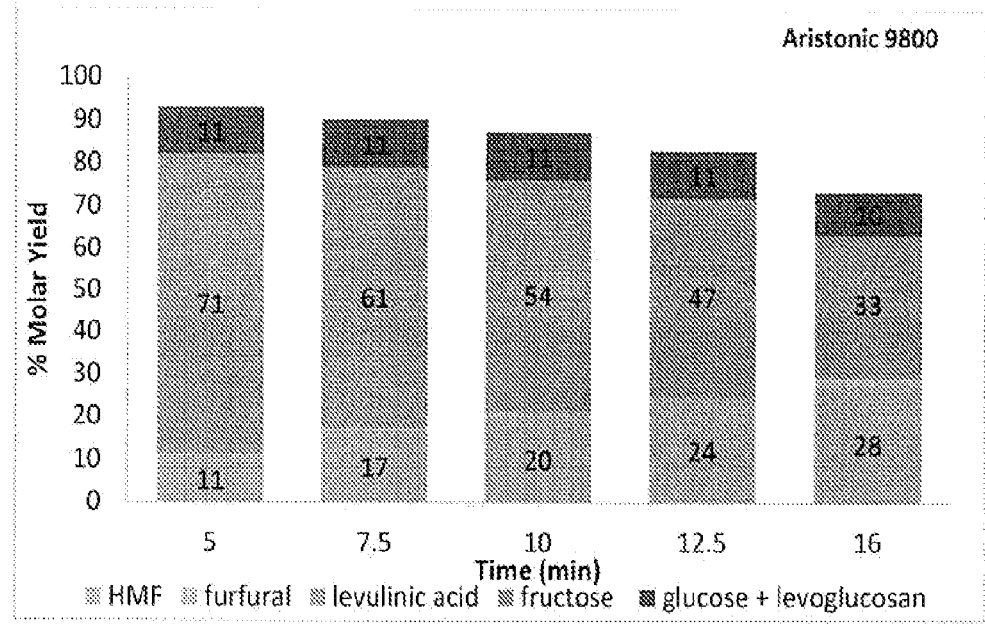
FIGS. 5A and 5B show the compositions of the products generated in connection with FIGS. 3A and 3B at various reaction times, and in additional testing at other reaction times, using two grades of Aristonic® acid (the one used in producing FIGS. 3A and 3B, and one other).
Figure 5B:
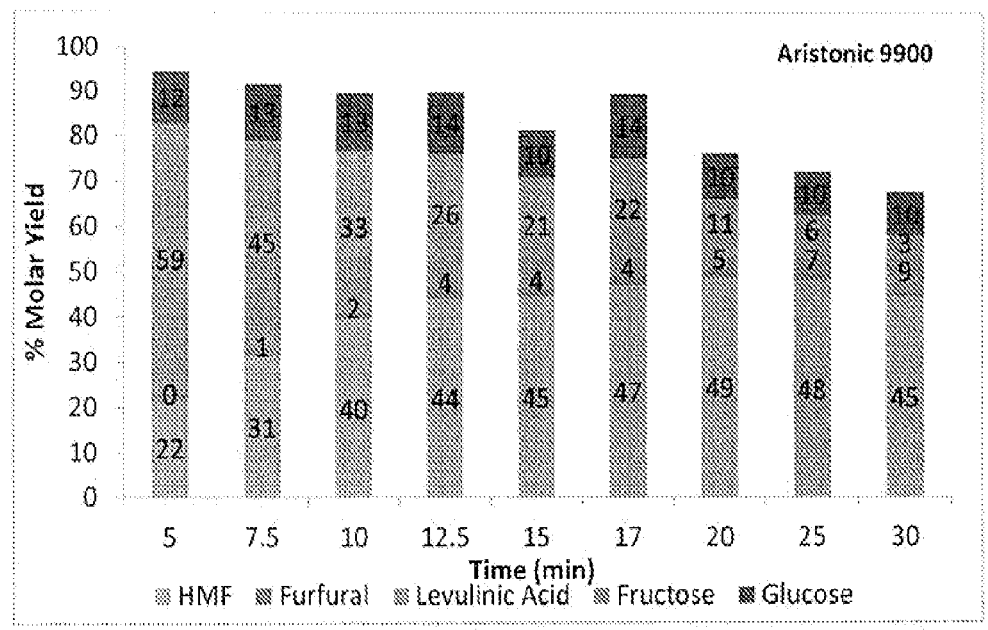

A more detailed compositional analysis was conducted of the dehydration product mixtures that resulted at various reaction times in Examples 5-9 using the Aristonic® acid 9800 grade catalyst. An analysis was also conducted on the product mixture resulting from use of the same catalyst and according to the same method of Examples 5-9, but with a longer, 16 minute reaction/residence time. These results are shown in FIG. 5A. For comparison, a series of tests were conducted in the same manner at various reaction times, but using an Aristonic® acid 9900 grade catalyst from the same manufacturer. The detailed compositional analyses of the product mixtures produced are shown in FIG. 5B, and demonstrate higher HMF yields and overall sugar accountabilities for the 9900 grade material as compared to the 9800 grade material.

Examples 11 and 12

Figure 6A:
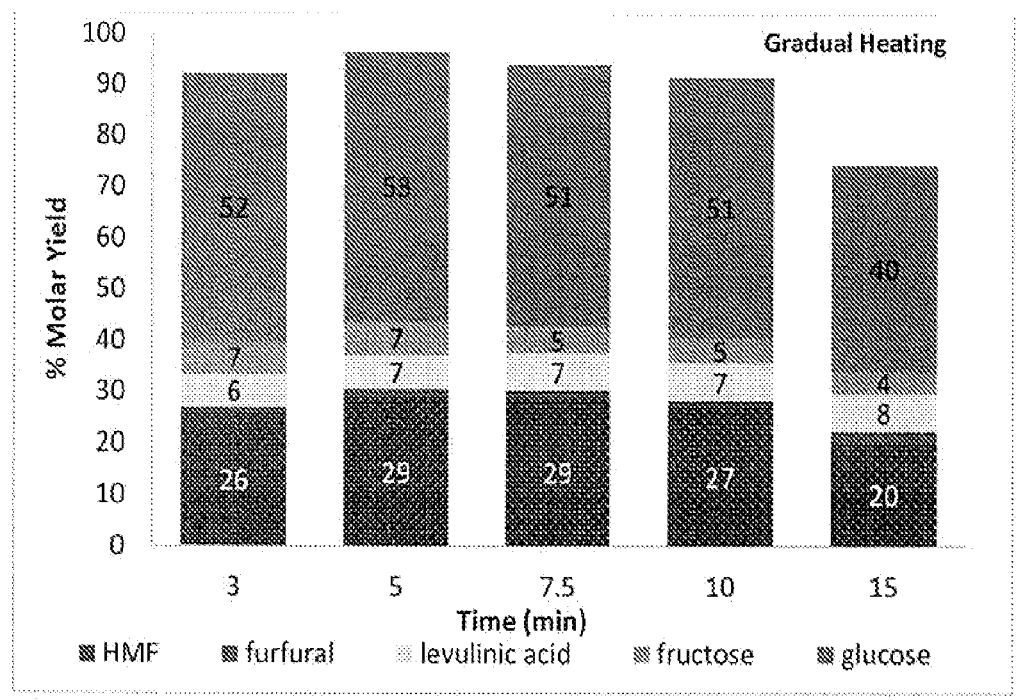
FIGS. 6A and 6B show the differences in product composition and overall sugar accountability produced by using gradual or fast heating of the hexose sugar solution at several reaction times, in dehydrations using a particular substituted sulfonic acid material.
Figure 6B:
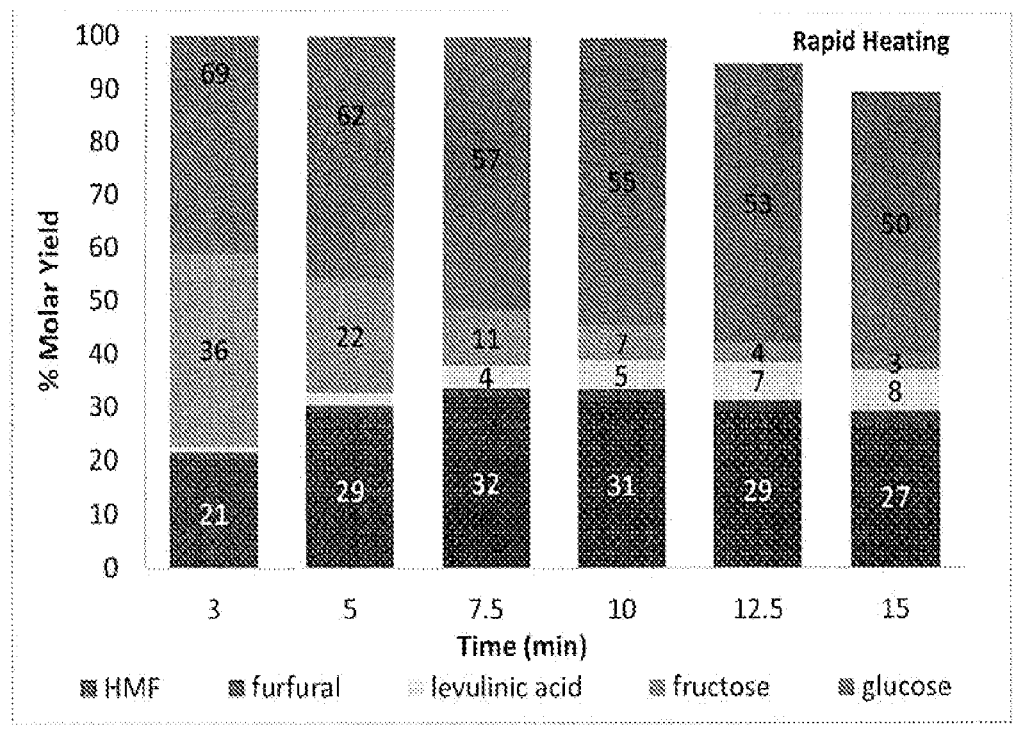

Further experiments were conducted using the same 75 mL Parr reactor arrangement, to determine the effect of rapid feeding/heating versus gradual heating on sugar conversion and HMF yield. An aqueous HFCS 42 solution (corresponding to 10% of combined sugars on a dry solids basis) was dehydrated at 180 degrees Celsius for various reaction times, using a 2% loading by weight of the total sugars of 6-amino-m-toluenesulfonic acid (ATSA). In one set of experiments, the aqueous HFCS 42 solution was combined with the ATSA, and gradually heated over a period of 25 minutes to the 180 degree Celsius reaction temperature, before holding that temperature for the indicated additional 3, 5, 7.5, 10 or 15 minutes. Detailed compositional analysis of the product mixtures that resulted produced FIG. 6A. In another set of experiments, the aqueous HFCS 42 solution was rapidly fed over about 120 seconds to a preheated reactor containing the catalyst, and the reaction continued after addition for the further 3, 5, 7, 5, 10, 12.5 and 15 minutes. After rapidly cooling the product mixture in keeping with Examples 5-9 and 10, detailed compositional analysis of the product mixtures at these various reaction times produced FIG. 6B.

Examples 13-15

Figure 7A:
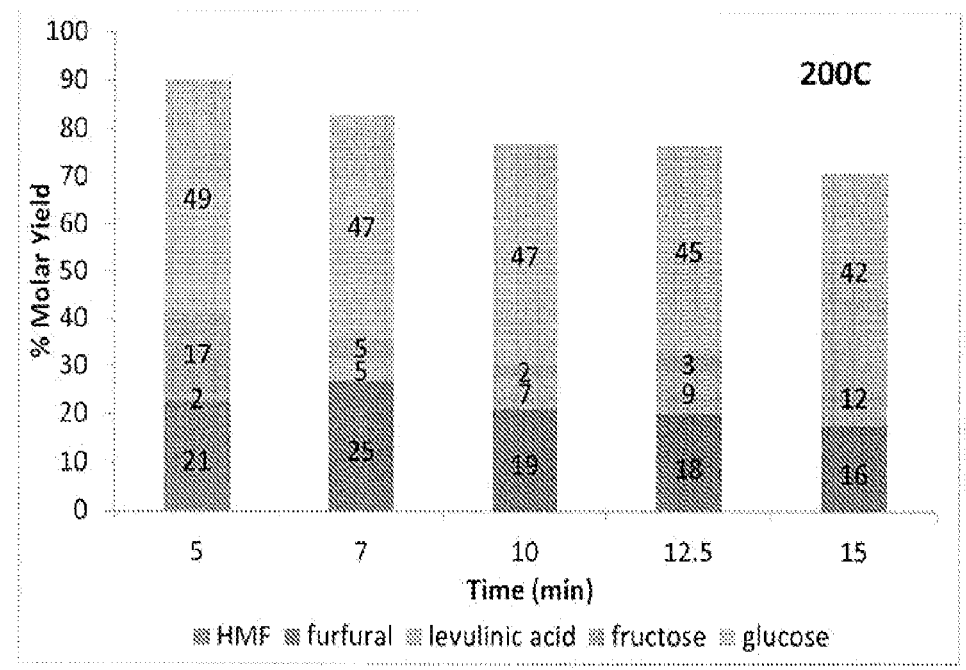
FIGS. 7A-7C show the differences in product composition and overall sugar accountability produced at various reaction temperatures using a particular catalyst on a particular feed, at various reaction times.
Figure 7B:
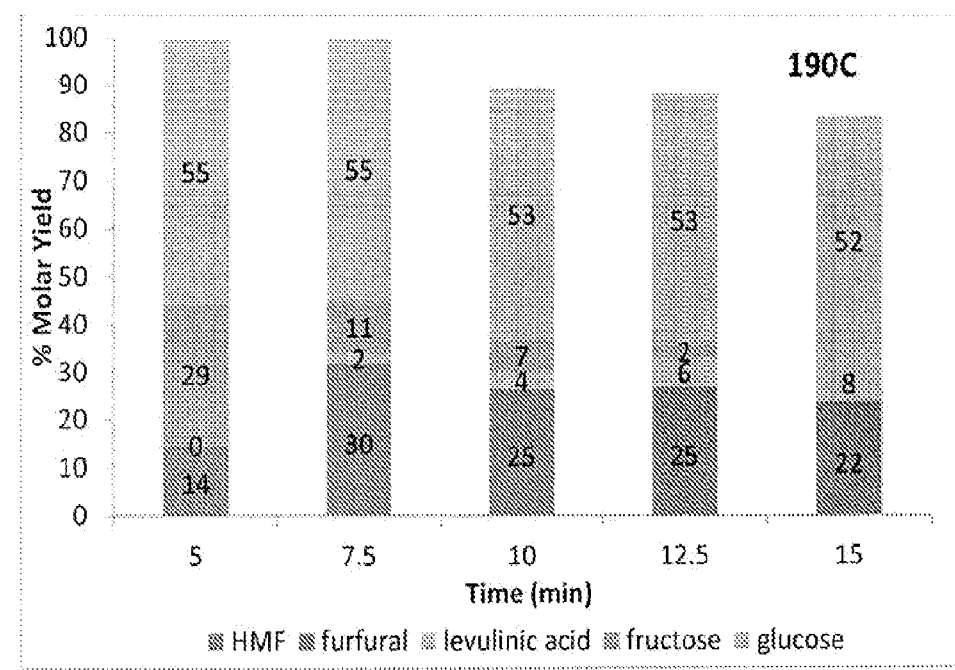
Figure 7C:
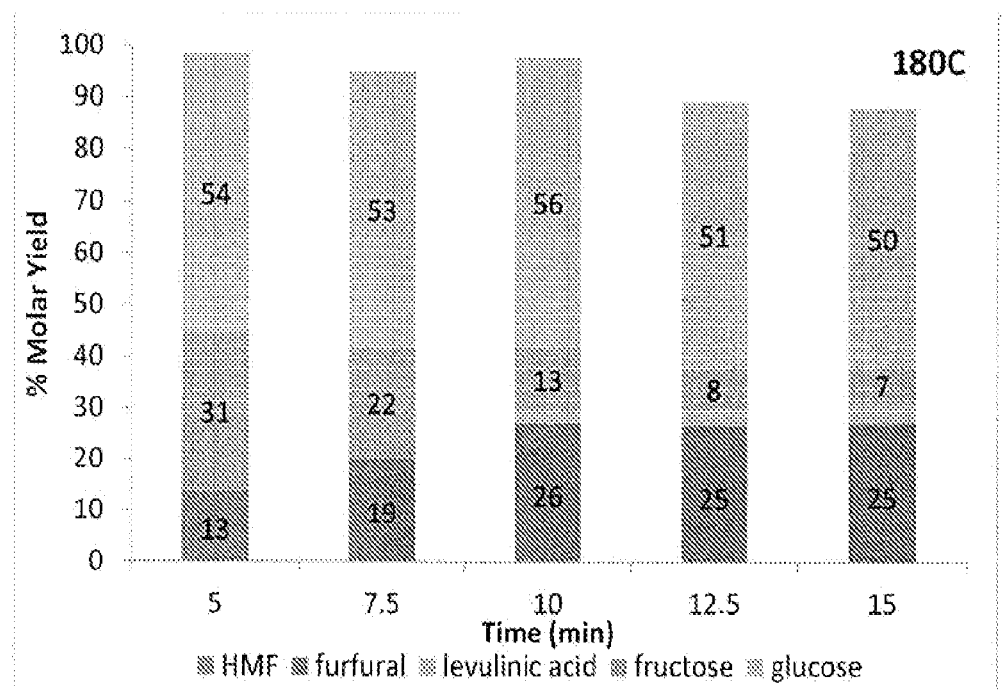

Three studies were conducted of the effect of the reaction temperature on the dehydration of an aqueous HFCS 42 sugar solution using the Calsoft® LAS-99 linear alkylbenzene sulfonic acid catalyst at the same 5, 7.5, 10 and 12.5 minute reaction/residence times, in terms of overall sugars accountability and product composition. One series of experiments was conducted at these residence times and 180 degrees Celsius, while additional series were conducted at 190 and 200 degrees Celsius reaction temperatures. The same 13% dry solids basis HFCS 42 solution was used, with the catalyst being present at 2% by weight of the total sugars. The sugar solution in each run was fed in rapidly over 60 seconds. The results are shown in FIGS. 7A, 7B and 7C.

Examples 16-23

A series of experiments were carried out with a 2% loading by weight of 6-amino-m-toluenesulfonic acid (ATSA) on various combinations of fructose and glucose at the same sugars concentration, reaction temperature and time, with rapid feeding/heating of the sugars feed over the same feed cycle time, to assess the effect on product composition and overall sugars accountability especially from using various commercially available combinations of fructose and glucose. Subsequently, a series of further experiments were conducted under the same conditions with the aqueous HFCS 90 solution, except that the reaction/residence time was varied.

Figure 8A:
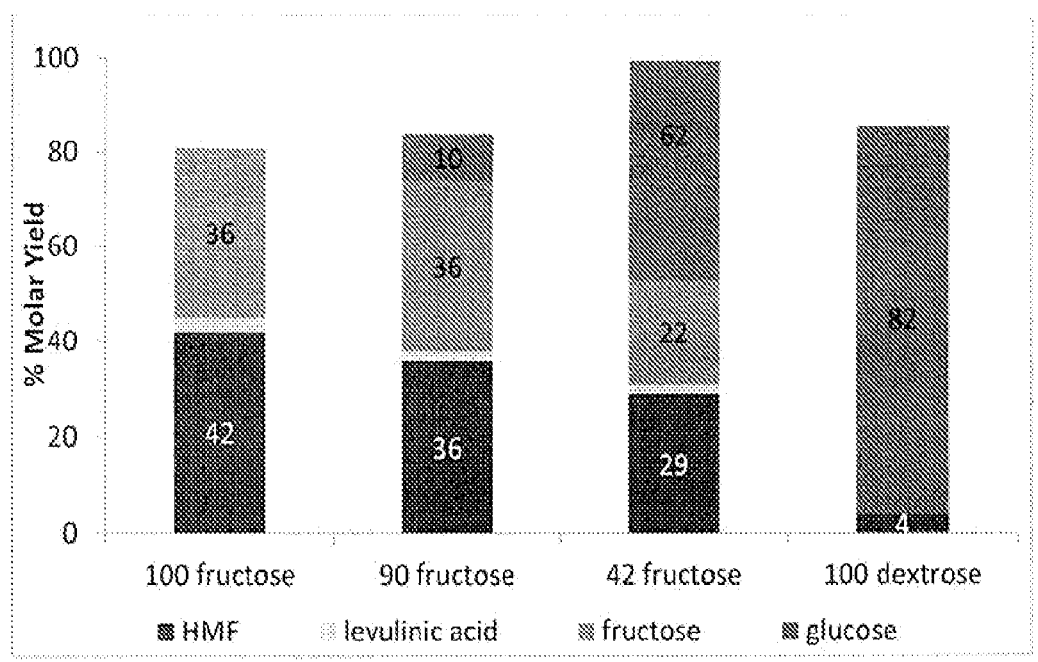
FIGS. 8A and 8B show the compositional differences in the products generated by dehydrating various combinations of fructose and glucose under identical conditions and using a particular substituted sulfonic acid catalyst (8A), or generated from a particular combination of fructose and glucose with the same sulfonic acid catalyst, but different reaction times (8B).

In the first series, aqueous solutions of fructose only, glucose only, HFCS 42 and HFCS 90 products, all at 13% total sugars on a dry solids basis, were rapidly fed over 60 seconds into the 75 mL Parr reactor setup, which had been preheated with the solubilized ATSA catalyst (in aqueous solution) to 180 degrees Celsius. After 5 minutes, the reactor contents were withdrawn, rapidly cooled as in previous examples, and analyzed by HPLC. The results of the first series are presented in FIG. 8A.

Figure 8B:
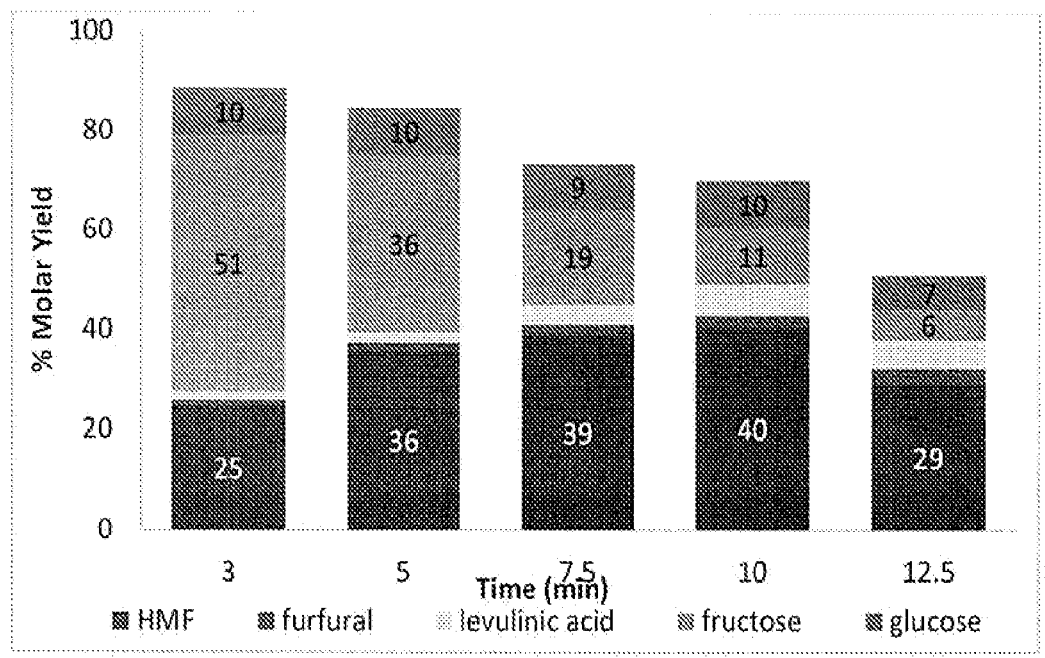

For the HFCS 90-based series, the same dehydration reactions were carried out at 3, 7.5, 10 and 12.5 minute reaction/residence times, for comparison to the run from the first series at a 5 minute reaction/residence time. These results are presented in FIG. 8B.

Examples 24-27

These examples were conducted to investigate whether yields of dehydration products could be improved over those shown in the preceding Examples 16-23 for a glucose only sugars solution, through using higher loadings of the ATSA catalyst. Experiments were also conducted in the absence of any catalyst for comparison, and at two reaction temperatures (165 degrees Celsius and 180 degrees Celsius as employed in Examples 16-23). One notable difference from the glucose only. 2% ATSA experiment in Examples 16-23 is that for these Examples, the sugars solution was combined with the catalyst from the start, and the mixture was gradually heated to the reaction temperature. In addition, a 5% solution was used of the glucose rather than the 13% solution of Examples 16-23 (on a dry solids basis in each case), and a longer thirty minute reaction/residence time was used. With these differences noted, the results are shown below in Table 1:

TABLE 1

| Entry # | Temp C. | % ATSA catalyst | % Molar Yield | | | | |
| | | | HMF | furfural | levulinic acid | total known | glucose |
| --- | --- | --- | --- | --- | --- | --- | --- |
| 1 | 180 | 0.0 | 6 | 1 | 0 | 92 | 86 |
| 2 | 180 | 2.4 | 12 | 1 | 1 | 80 | 67 |
| 3 | 180 | 4.8 | 11 | 1 | 0 | 62 | 49 |
| 4 | 165 | 0.0 | 2 | 0 | 0 | 93 | 91 |
| 5 | 165 | 2.4 | 7 | 0 | 0 | 78 | 70 |
| 6 | 165 | 4.4 | 9 | 0 | 2 | 71 | 60 |

Reaction conditions: 2% ATSA at 180° C. with 5% DS glucose, 30 min, 25 min gradual heating.

As may be observed from Table 1, at 180 degrees Celsius and 2.4% catalyst loading, 33% of the glucose was converted but HMF was produced at a yield of only 12 molar percent. By doubling the catalyst loading, glucose conversion rose to 51 percent, but HMF molar yield was relatively the same. Similar effects were seen at 165 degrees Celsius reaction temperature. The catalyzed reactions performed substantially better that the "no catalyst" runs.

Examples 28-32

Experiments were conducted with 2% loadings (in relation to the total mass of sugars) of several inventive substituted sulfonic acid catalysts alongside runs with 0.5 percent of sulfuric acid. Aqueous sugar solutions of HFCS 42 and HFCS 90 products were used at the concentrations indicated in Table 2 below, with rapid feeding/heating in all cases over a feed cycle between 1 and 2 minutes in duration to the preheated 75 mL Parr reactor arrangement containing the solubilized sulfonic acid catalyst or the sulfuric acid catalyst, as the case may be. Other conditions were as indicated in Table 2:

TABLE 2

| Starting syrup (% fructose) | Catalyst | Reaction time (min) | temp (C.) | Dry solids (%) | % molar yield | | | | |
|---|---|---|---|---|---|---|---|---|---|
| | | | | | HMF | Furfural | Levulinic acid | Hexoses | Total known |
| 42 | 0.5% H$_2$SO$_4$ | 5 | 196 | 15 | 32 | 2 | 4 | 58 | 96 |
| 42 | 2% ATSA | 5 | 180 | 16 | 24 | 1 | 2 | 75 | 91 |
| 42 | 2% ATSA | 7.5 | 180 | 10 | 32 | 1 | 4 | 68 | 100 |
| 90 | 0.5% H$_2$SO$_4$ | 7 | 185 | 10 | 51 | 2 | 2 | 41 | 95 |
| 90 | 2% ATSA | 5 | 180 | 13 | 38 | 2 | 2 | 46 | 88 |
| 90 | 2% LAS | 7.5 | 180 | 13 | 42 | 2 | 3 | 40 | 88 |
| 90 | 2% ATSA | 10 | 180 | 8 | 63 (8)[1] | 2 | 1 | 20 | 94 |

[1]Performed in 1.3:1 EtOH:H2O; 8% noted with ethoxymethylfurfural (EMF)

Examples 33-36

Experiments were carried out, based on the indication in the last of the immediately preceding examples that inclusion of ethanol improved hexose conversion and increased overall sugars accountability, to study the effect of performing the dehydration in mixtures of an alcohol (such as ethanol) and water instead of just water. For these examples, an aqueous sugars solution comprised of HFCS 90 (15% on a dry solids basis) was rapidly fed to the 75 mL Parr reactor containing a 2% loading of ATSA in water or in a combination of ethanol and water at 180 degrees Celsius. After 10 minutes following the completion of the feed cycle, the products were withdrawn, rapidly cooled as in previous examples and analyzed by HPLC, with the product compositions and percentage molar yields indicated in FIG. 9A.

Examples 37-41

The same aqueous sugars solution as used in Examples 33-36 was fed and dehydrated just as described in Examples 33-36, except that the reaction time was varied and a consistent ethanol:water ratio was employed at 1.3:1. The product compositions produced and the percentage molar yields of the various materials found in the product mixtures, whether dehydration products or unconverted sugars, were as shown in FIG. 9B.

Figure 9A:
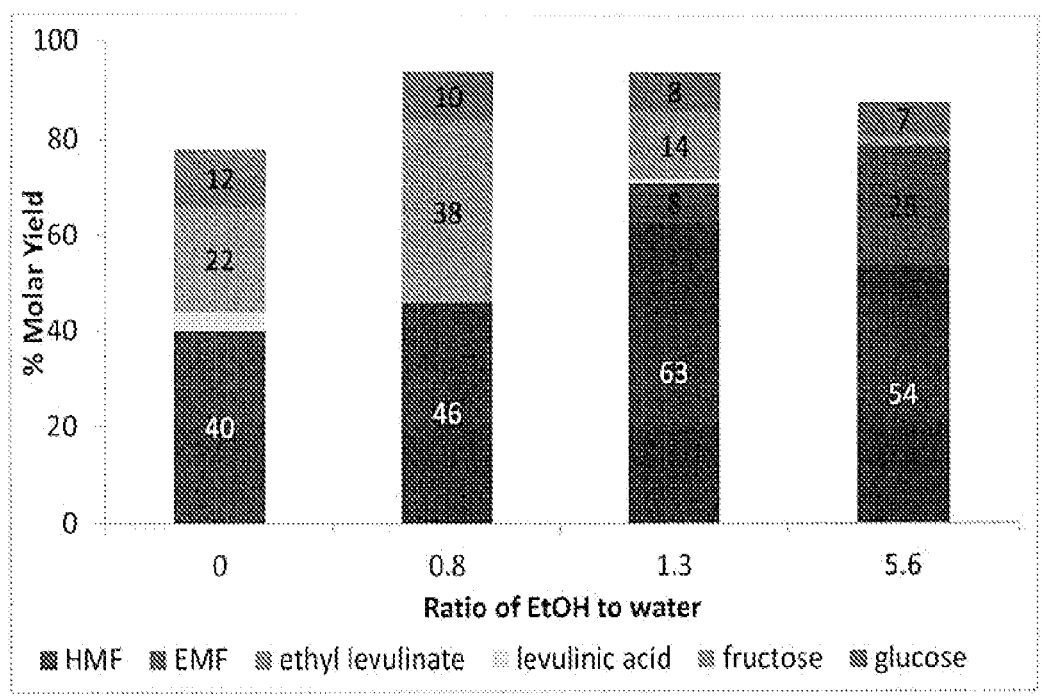
FIGS. 9A and 9B show the product compositions resulting from rapid heating of a particular sugar solution and with using a particular substituted sulfonic acid, sugar dehydration catalyst, where ethanol is present in various ratios with water (9A) or at a given ratio with water but at various reaction times (9B).
Figure 9B:
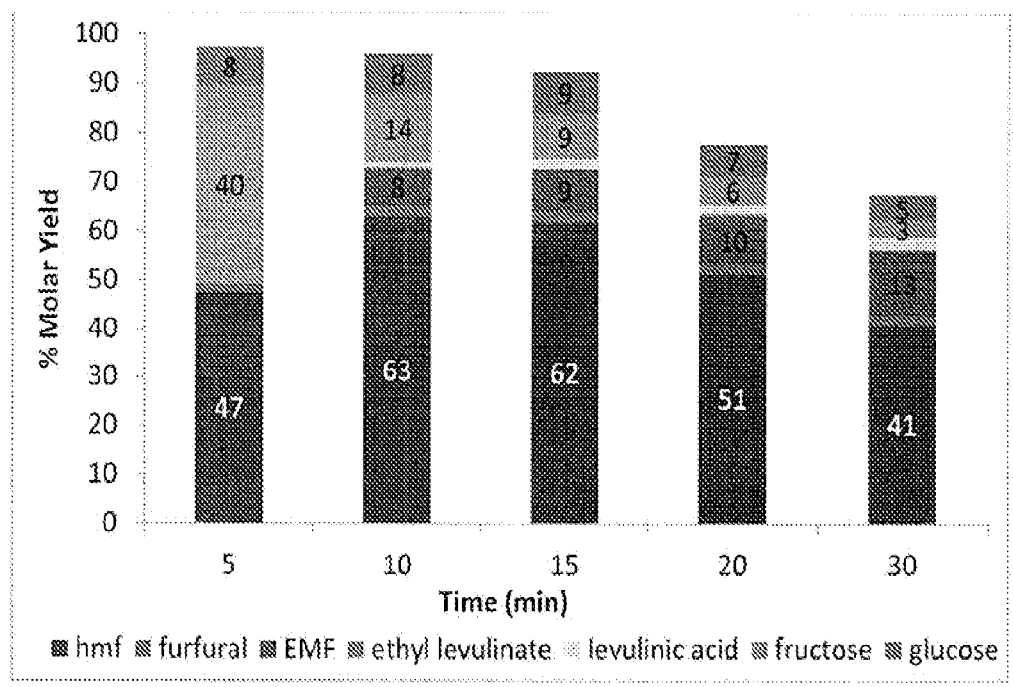

The results shown in FIGS. 9A and 9B collectively indicate that the amount of sugars converted, product yields and overall sugars accountability can be influenced by a selection of the reaction time and of the ratio of ethanol to water. Thus, when the ethanol to water ratio was varied from 0 to 1.3:1, HMF yield increased from 40% to 63% at 10 minutes reaction time, and sugar accountabilities increased from 79% to 95%. Ethoxymethylfurfural (EMF) was also produced in 8-9% molar yield, providing an overall furan yield of 71% at 10 and 15 min with >90% sugar accountability. An even higher ratio of ethanol to water (5.6:1) showed the highest furan yield of 79% (FIG. 9A). With respect to FIG. 9B, at a given ethanol: water ratio, EMF yield increased with time as the sugar accountability decreased.

Examples 42-44

The ability to separate out and recover both unreacted sugars and the sulfur-containing catalyst is an important commercial consideration. Solvent extractions of a dehydration product mixture including solubilized Calsoft® LAS-99 linear alkylbenzene sulfonic acid catalyst were conducted with diethyl ether, methyl tert-butylether and hexane in turn. Each of the solvents was combined with an equal mass of the product mixture including the solubilized catalyst, and shaken in a test tube at ambient temperature. The mixture was then centrifuged at 3000 rpm for 20 minutes. After allowing the aqueous and organic phases to phase-separate, the two phases were then analyzed by HPLC and by ICP using internal standards to determine how HMF and the solubilized, sulfur-containing catalyst partitioned themselves between the aqueous and organic phases. More particularly, sulfur was analyzed following dilution in 2% nitric acid via ICP for sulfur at 180.731 nm using an internal standard. Results of the HPLC and ICP analyses are shown in Table 3 as follows (the unreacted sugars remained with the aqueous phase):

TABLE 3

| Organic Solvent | % Organic Solvent* | % HMF | | % sulfur | |
|---|---|---|---|---|---|
| | | aqueous | organic | aqueous | organic |
| diethyl ether | 60 | 67 | 45 | 41 | 62 |
| MTBE | 60 | 49 | 47 | 23 | 66 |
| Hexane | 51 | 100 | 0 | 97 | 8 |

*% organic solvent = (wt solvent)/(wt solvent + wt reaction mix) * 100

Examples 45-48

The same apparatus and procedures as used in Examples 42-44 were used for the solvent extraction of product mixtures including ATSA, except that two different combinations of ethyl acetate with the product mixture were evaluated (at two different proportions by weight in relation to the product mixture—48:52 and 31:69), along with methyl tetrahydrofuran (MTHF) and hexane at 50 percent by weight and 40 percent by weight, respectively. Results are shown in Table 4:

TABLE 4

| Organic Solvent | % Organic Solvent* | % sulfur | |
|---|---|---|---|
| | | aqueous | organic |
| ethyl acetate | 48 | 27 | 73 |
| ethyl acetate | 31 | 44 | 56 |
| MTHF | 50 | 38 | 62 |
| Hexane | 40 | 72 | 28 |

*% organic solvent = (wt solvent)/(wt solvent + wt reaction mix) * 100

Examples 49-52

Adsorption was also evaluated as a method for separating HMF from the solubilized, sulfur-containing catalyst and unreacted sugars. Three samples of product mixtures including solubilized Calsoft® LAS-99 linear alkylbenzene sulfonic acid catalyst were initially analyzed to determine the concentration of HMF therein, as well as the concentration of sulfur therein as indicative of solubilized catalyst content, by the same HPLC and ICP methods.

Weighed samples of the thus-analyzed product mixtures were then brought into contact with a quantity of LEWATIT® AF-5 carbon-based, spherical, microporous adsorption resin (Lanxess AG), and centrifuged therewith at 3000 rpm at ambient temperature for 20 minutes. Each liquid portion was decanted off, and analyzed for its HMF and sulfur content, to determine how much of the starting HMF and solubilized catalyst had been removed with the adsorbent. The used adsorbent was meanwhile washed twice with acetone as a desorption solvent for HMF, and the collected acetone wash liquid was analyzed for HMF content and for sulfur content, to determine how much of the HMF had been recovered from the adsorbent.

Details and results of the adsorption testing are found in Table 5.

TABLE 5

| starting solution | Adsorbent | wt starting solution g | wt of adsorbent g | % Reduction Sulfur % | HMF % |
|---|---|---|---|---|---|
| LAS rxn mix | Lewatit AF5 | 5.864 | 0.534 | 2.9 | 85.9 |
| LAS rxn mix | Lewatit AF5 | 5.877 | 0.562 | 8.1 | 87.0 |

As may be seen from Table 6 below, preliminary testing with AMBERLITE™ XAD-2™ and AMBERLITE™ XAD-4™ resins has indicated that it should also be possible to preferentially adsorb the solubilized sulfonic acid catalyst. Higher temperatures (45 degrees Celsius) seem to favor a greater adsorption of both the catalyst and HMF

TABLE 6

| starting solution | Adsorbent | Temp C. | % reduction Sulfur | HMF |
|---|---|---|---|---|
| LAS rxn mix | XAD2 | 45 | 76 | 26 |
| LAS rxn mix | XAD4 | 45 | 90 | 35 |
| LAS rxn mix | XAD2 | rt | 60 | 12 |
| LAS rxn mix | XAD4 | rt | 80 | 25 |

LAS99 rxn mixture containing 3.26% HMF and 10% adsorbent by wt of product mixture.

Example 53

Based upon the results of batch adsorption testing, a continuous flow adsorption test was completed on reaction product from the dehydration of an HFCS 90 sugars solution with Calsoft® LAS-99 linear alkylbenzene sulfonic acid catalyst.

Figure 10:
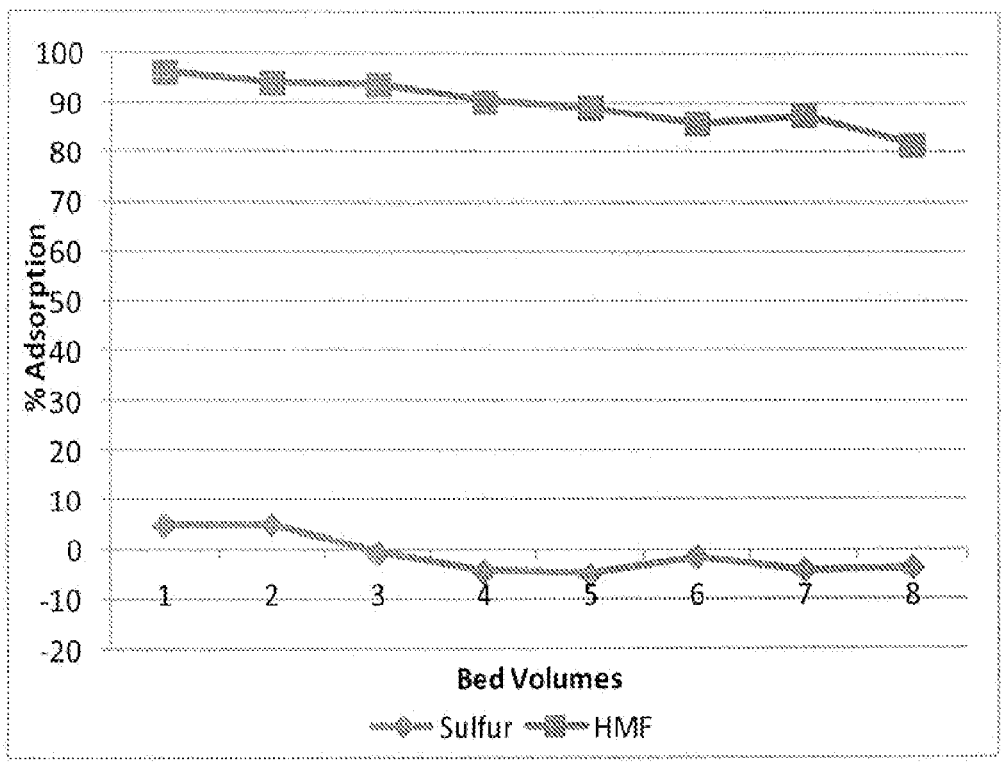
FIG. 10 shows the results of continuous flow through testing of an adsorbent for separating HMF from the residual sugars and solubilized substituted sulfonic acid catalyst, as a first step in recovering the HMF, the residual sugars for recycling or alternative uses, and the substituted sulfonic acid catalyst for reuse as desired.

A 25 mL adsorption column was prepared containing 15 mL of the LEWATIT® AF-5 carbon-based, spherical, microporous adsorption resin, and 50 mL of the reaction product was continuously pumped through the column at a rate of 1.5 mL/minute. The first sample was taken after 33 minutes, after three bed volumes of material had flowed through the adsorbent, and then at 10 minute/additional bed volume intervals thereafter. The samples thus taken were analyzed for HMF and sulfur as in the previous examples, with the results shown in FIG. 10.

Examples 54-59

These examples illustrate the use of solids/liquid separation methods such as filtration for removing the solubilized sulfonic acid catalyst from the product mixture (or from the remainder of a product mixture, after HMF has been largely removed, for example, by adsorption with LEWATIT® AF-5 carbon-based, spherical, microporous adsorption resin (Lanxess AG) as just shown).

Calcium hydroxide contains water-soluble calcium which reacts with sulfate ions to form insoluble calcium sulfate salts. Other materials, such as calcium chloride, for example, may be considered as well, though calcium chloride would generate hydrochloric acid and so would be viewed as less preferred.

Experiments were accordingly performed with calcium hydroxide in the batch mode, to evaluate the effectiveness of adding this material for sulfur removal to product mixtures containing solubilized substituted sulfonic acid catalysts and whose beginning sulfur contents were determined by ICP. Various molar equivalents of calcium hydroxide to sulfur were tested, with centrifugation at 3000 rpm for 20 minutes at ambient temperature, followed by filtration to isolate the filterable solids that were formed. Solutions of certain of the catalysts in ambient and above-ambient water (without sugars or HMF) were also prepared for comparison, and the calcium hydroxide was added to these with subsequent centrifugation, filtration and sulfur testing as with the product mixtures.

The results with the product mixtures are given in Table 7 below:

TABLE 7

| Entry | starting solution | equivalents of calcium source to sulfur mol % | sulfur reduction from initial % |
|---|---|---|---|
| 1 | EM-99 reaction mix | 12 | 82 |
| 2 | LAS-99 reaction mix | 10 | 82 |
| 3 | LPS-99 reaction mix | 10 | 68 |
| 4 | EM-99 heated standard | 3 | 86 |
| 5 | LPS-99 standard ambient | 1 | 84 |
| 6 | LPS-99 heated standard | 9 | 86 |

Examples 60-64

For these examples a series of reactions were carried out using Calsoft® LAS-99 linear alkylbenzene sulfonic acid catalyst on the one hand, and the conventional sulfuric acid catalyst on the other, at equivalent acid strengths of 0.05 grams sulfuric acid equivalents per gram of sugars, in order to compare the effectiveness of each in producing levulinic acid from an aqueous glucose solution.

For each run, the sulfuric acid or solubilized sulfonic acid was combined in the 75 mL Parr reactor with water, and with about 0.13 grams of $AlCl_3$ per gram of sugars added to promote isomerization of glucose to fructose. The combination was preheated to a reaction temperature of 180 degrees Celsius, and an aqueous glucose solution was pumped into the reactor over a period of twenty minutes. After the indicated reaction/residence times in Table 8 below, the product mixture was withdrawn, rapidly cooled as in previous examples, and then analyzed by HPLC. Results are shown in Table 8, and demonstrate that the sulfonic acid produced more levulinic acid and greater overall sugar accountabilities than the conventional sulfuric acid, at an equivalent acid strength.

TABLE 8

| Sample # | Reaction time (min) | % molar yield | | | | | Dry solids in reactor |
|---|---|---|---|---|---|---|---|
| | | HMF | furfural | levulinic acid | Total knowns | glucose + levoglucosan | |
| H2SO4-1 | 5 | 12 | 1 | 21 | 44 | 10 | 9.2 |
| H2SO4-2 | 7 | 9 | 1 | 23 | 35 | 2 | 9.2 |
| H2SO4-3 | 10 | 7 | 1 | 24 | 33 | 0 | 9.2 |
| H2SO4-4 | 12 | 5 | 1 | 24 | 32 | 2 | 9.2 |
| H2SO4-5 | 15 | 3 | 1 | 22 | 26 | 0 | 9.2 |
| LAS-1 | 5 | 8 | 1 | 38 | 56 | 9 | 11 |
| LAS-2 | 7 | 7 | 1 | 39 | 64 | 17 | 11 |
| LAS-3 | 10 | 3 | 1 | 44 | 48 | 0 | 11 |
| LAS-4 | 12 | 2 | 1 | 46 | 49 | 0 | 11 |
| LAS-5 | 15 | 1 | 0 | 46 | 47 | 0 | 11 |

Examples 65-69

For these examples a series of reactions were carried out using Calsoft® LAS-99 linear alkylbenzene sulfonic acid catalyst on the one hand, and the conventional sulfuric acid catalyst on the other, at equivalent acid strengths of 0.003 grams sulfuric acid equivalents per gram of sugars, in order to compare the effectiveness of each in producing HMF from an aqueous fructose 42 solution.

For each run, the sulfuric acid or solubilized sulfonic acid was combined in the 75 mL Parr reactor with water. The combination was preheated to a reaction temperature of 180 degrees Celsius, and an aqueous fructose 42 solution (20% DS) was pumped into the reactor over a period of 1 minute. After the indicated reaction/residence times in Table 9 below, the product mixture was withdrawn, rapidly cooled as in previous examples, and then analyzed by HPLC. Results are shown in Table 9, and demonstrate that the sulfonic acid produced more HMF and greater overall HMF selectivity than the conventional sulfuric acid, at an equivalent acid strength.

Example 70

An aqueous solution of 6.52% fructose and 1.5% glucose recovered after adsorption of HMF (as described in example 53) was brought to 20% dry solids with the addition of HFCS 90. The solubilized sulfonic acid was combined in the 75 mL Parr reactor with water, and the combination preheated to a reaction temperature of 180 degrees Celsius. An aqueous solution of recycled sugars with HFCS 90 was pumped into the reactor over a period of 2.5 minutes. After the indicated reaction/residence times in Table 10 below, the product mixture was withdrawn, rapidly cooled as in previous examples, and then analyzed by HPLC. Results are shown in Table 10, and demonstrate that the recovered sugars can likewise be used to produce HMF.

TABLE 9

| sample # | Reaction time (min) | % molar yield | | | | | | % HMF selectivity* |
|---|---|---|---|---|---|---|---|---|
| | | HMF | furfural | levulinic acid | total knowns | fructose | glucose + levoglucosan | |
| LAS-1 | 5 | 13 | 1 | 0 | 98 | 31 | 54 | 83 |
| LAS-2 | 7.5 | 19 | 1 | 0 | 95 | 22 | 53 | 77 |
| LAS-3 | 10 | 26 | 1 | 2 | 98 | 13 | 56 | 83 |
| LAS-4 | 12.5 | 25 | 2 | 3 | 89 | 8 | 51 | 62 |
| LAS-5 | 15 | 25 | 2 | 4 | 88 | 7 | 50 | 46 |
| H2SO4-1 | 5 | 9 | 0 | 0 | 99 | 36 | 53 | 86 |
| H2SO4-2 | 7.5 | 15 | 1 | 0 | 95 | 27 | 52 | 72 |
| H2SO4-3 | 10 | 17 | 1 | 0 | 92 | 23 | 51 | 65 |
| H2SO4-4 | 12.5 | 18 | 1 | 1 | 86 | 18 | 48 | 54 |
| H2SO4-5 | 15 | 20 | 1 | 1 | 79 | 15 | 41 | 35 |

180 C., $3.0 \times 10^{-3}$ g H2SO4 equiv per g sugar, 13% final DS.
*HMF selectivity = (moles HMF produced/moles reacted sugars) * 100

TABLE 10

| sample # | Reaction time (min) | HMF | furfural | levulinic acid | Total knowns | fructose | glucose + levoglucosan |
|---|---|---|---|---|---|---|---|
| 1 | 5 | 24 | 1 | 0 | 94 | 55 | 14 |
| 2 | 7.5 | 32 | 1 | 2 | 87 | 37 | 15 |
| 3 | 10 | 41 | 2 | 4 | 84 | 22 | 15 |
| 4 | 12.5 | 37 | 2 | 5 | 73 | 5 | 14 |
| 5 | 5 | 41 | 3 | 8 | 77 | 11 | 15 |

% molar yield

Conditions: 180 C., 14% final DS, 1% LAS99 catalyst by wt of sugars in.

Examples 71-77

To illustrate one method for separating the substituted sulfonic acid catalysts of the present invention, a solubilization study was initially performed with the addition of 0.1 g of a selected sulfonic acid to 10 g of water. The mixture was shaken in a test tube at ambient temperature and then centrifuged at 3000 rpm for 20 minutes. The liquid portion was then analyzed by ICP to determine how much of the sulfur-containing catalyst solubilized in water. A second solubilization study was then performed with the preparation of a standard solution of 0.8 g fructose, 0.8 g of HMF, in 80 g of water. To 10 mL of this solution was added approximately 100 mg of each catalyst. Each sample was centrifuged for 20 min at 3000 rpm and then analyzed. Results of the ICP analyses are shown in Table 11 as follows.

TABLE 11

| Entry # | catalyst | Sulfur in water % of initial | Sulfur in water/HMF/fructose % of initial |
|---|---|---|---|
| 1 | Aristonic ® 9800 | 3.9 | 3.6 |
| 2 | DNSA | 18.9 | 21.6 |
| 3 | Aristonic ® 9900 | 36.1 | 30.9 |
| 4 | ATSA | 42.0 | 55.3 |
| 5 | pTSA* | 95.3 | 100 |
| 6 | EM99 | 99.1 | 100 |
| 7 | LAS99 | 100.1 | 96.3 |
| 8 | LPS99 | 100.0 | 85.1 |

*p-toluenesulfonic acid - not a catalyst of the present invention

Based on the solubility testing, a series of solutions of about 150 mg of catalyst in 6.65 grams water were prepared, to which was added 40 mg $Ca(OH)_2$ in order to form a calcium salt. After centrifuging at 3000 rpm for 20 minutes, the liquid portion was analyzed to determine how much of the catalyst remained solubilized in water and how much had been removed in a filterable solid mass. Results are shown in Table 12 below:

TABLE 12

| Catalyst | Sulfur, % In water |
|---|---|
| Aristonic ® 9900 | 69.3 |
| Aristonic ® 9800 | 10.0 |
| LPS 99 | 14.5 |
| LAS 99 | 9.7 |
| EM 99 | 15.4 |
| DNSA | 16.4 |
| ATSA | 100 |
| p-TSA* | 100 |

*p-TSA not according to present invention

Examples 78-84

An aqueous solution of 1.034 g fructose, 1.043 g HMF, and 99.17 g water was prepared. Eight different tests were performed with the addition of 5 grams of the aqueous solution to about 5 milliliters of MTBE and a sulfonic acid catalyst (in the amounts indicated below). Each mixture was centrifuged at 3000 rpm for 15 minutes at ambient temperature. Several of the mixtures showed an interface but not a particularly clean separation of the aqueous and organic phases, while for the mixture containing the Aristonic® 9900 catalyst there was not much of a clear organic phase. Consequently, the weights of the organic phases reported in Table 13 following are approximate. With this caveat, the organic layers were collected and analyzed for sulfur and HMF, and the aqueous layers were collected and analyzed for HMF, sulfur and fructose. The results are shown in Table 13:

TABLE 13

| | | | Organic Phase | | Aqueous Phase | | | Recovery of Initial Components | | |
|---|---|---|---|---|---|---|---|---|---|---|
| Entry # | catalyst | Catalyst weight (mg) | HMF % of initial | Sulfur % of initial | HMF % of initial | Fructose % of initial | sulfur % of initial | HMF % | fructose % | sulfur % |
| 1 | EM99 | 88 | 18 | 6 | 87 | 116 | 69 | 105 | 116 | 75 |
| 2 | LAS99 | 50 | 6 | 4 | 86 | 107 | 66 | 91 | 107 | 71 |
| 3 | Aristonic 9800 | 54 | 17 | 4 | 86 | 109 | 7 | 103 | 109 | 12 |
| 4 | LPS99 | 70 | 20 | 10 | 85 | 106 | 45 | 105 | 106 | 55 |
| 5 | Aristonic 9900 | 60 | na | 12 | 86 | 104 | 36 | 86 | 104 | 48 |
| 6 | DNSA | 69 | 17 | 1 | 83 | 104 | 7 | 100 | 104 | 9 |
| 7 | ATSA | 56 | 14 | 0 | 95 | 113 | 57 | 109 | 113 | 57 |
| 8 | pTSA* | 59 | 15 | 1 | 94 | 111 | 80 | 109 | 111 | 81 |

*not a substituted sulfonic acid of the present invention.

Examples 85-89

Batchwise sugar alcohol dehydrations were performed at bench scale. For these examples, the apparatus and procedure of Examples 1-4 were used, except that the reaction chamber was charged with a concentrated sorbitol solution (45.5 g of 61% sorbitol by wt) and with a selected substituted sulfonic acid catalyst at a loading of 1.20% g sulfuric acid equivalents per g of alcohol. In each instance, the sugar alcohol solutions were then dehydrated over a further thirty (30) minutes at a temperature of 170 degrees Celsius. The results are shown in Table 14 for the molar percentage yields of sorbitans, isosorbide, and sugar alcohols.

TABLE 14

| Catalyst | % molar yield | | | | | |
|---|---|---|---|---|---|---|
| | 2,5-Sorbitan | 1,4-sorbitan | Isosorbide | Mannitol | total known | Sorbitol |
| H2SO4 | 2 | 43 | 6 | 1 | 79 | 26 |
| ATSA | 1 | 19 | 1 | 1 | 96 | 74 |
| LAS 99 | 13 | 64 | 11 | 0 | 98 | 11 |
| EM 99 | 13 | 63 | 11 | 0 | 98 | 11 |
| Aristonic ® 9800 | 2 | 35 | 4 | 1 | 100 | 58 |
| Aristonic ® 9900 | 3 | 59 | 8 | 0 | 92 | 22 |
| p-TSA* | 3 | 61 | 12 | 0 | 88 | 11 |
| Methanesulfonic acid* | 1 | 18 | 1 | 1 | 97 | 77 |

Reaction conditions: 170° C., 30 min reaction time, gradual heating over 20 min, loading of 65% sorbitol solution, 1% sulfuric acid equivalent per g sugar alcohol, 850 rpm.
*Not a substituted sulfonic acid of the present invention

What is claimed is:

1. A process for making one or more sugar dehydration products from an aqueous sugars solution including one or more of pentoses and hexoses, comprising subjecting the aqueous sugars solution to an acid-catalyzed dehydration at an elevated temperature using a substituted sulfonic acid catalyst selected from the group consisting of dinonylnaphthalene sulfonic acid, 6-amino-m-toluenesulfonic acid, linear alkylbenzene sulfonic acid, and branched alkylbenzene sulfonic acid.

2. A process according to claim 1, wherein the dehydration is carried out to produce a product mixture including the one or more sugar dehydration products and further including residual sugars.

3. A process according to claim 2, further comprising separating residual sugars from the one or more sugar dehydration products, and separating out substituted sulfonic acid catalyst from residual sugars and one or more sugar dehydration products.

4. A process according to claim 3, further comprising using at least a portion of the residual sugars directly in an ethanol fermentation, in a fermentation to produce lysine, in a fermentation to produce lactic acid, or as a feed in a process for making a sugar alcohol.

5. A process according to claim 3, further comprising recycling at least a portion of the residual sugars product to make additional of the one or more sugars dehydration products.

6. A process according to claim 1, wherein the sugars in the aqueous sugars solution are only one or more hexoses.

7. A process according to claim 6, wherein the aqueous sugars solution is an aqueous solution of glucose and fructose.

8. A process according to claim 7, wherein the glucose and fructose are present in the aqueous hexose solution in the same proportion as in an HFCS 42 corn syrup product, or an HFCS 55 corn syrup product, or an HFCS 90 corn syrup product.

9. A process according to claim 1, wherein the aqueous sugars solution is added to a reactor containing a substituted sulfonic acid catalyst and which has been preheated to the temperature at which the acid-catalyzed dehydration step is to be conducted.

10. A process according to claim 9, wherein the reaction temperature is from about 175 to about 205 degrees Celsius.

11. A process according to claim 10, wherein pressurized steam is injected into a reactor containing the aqueous sugars solution and directly heats the aqueous sugars solution to a temperature of from about 175 degrees Celsius to about 205 degrees Celsius.

12. A process according to any of claims 1, 9, 10 and 11, wherein the contents of the reactor following the dehydration are rapidly cooled to about 50 degrees Celsius and lower in not more than about 5 minutes.

13. A process according to claim 12, wherein the cooling is accomplished in about 3 minutes or less.

14. A process according to claim 1, wherein the aqueous sugars solution is heated from ambient temperature to a reaction temperature in less than about 30 minutes.

15. A process according to claim 14, wherein the aqueous sugars solution is heated from ambient temperature to the reaction temperature in less than about 10 minutes.

16. A process according to claim 15, wherein the aqueous sugars solution is heated from ambient temperature to the reaction temperature in less than about 8 minutes.

17. A process according to any of claims 14-16, wherein the contents of the reactor following the dehydration are rapidly cooled to about 50 degrees Celsius and lower in not more than about 5 minutes.

18. A process according to claim 17, wherein the cooling is accomplished in about 3 minutes or less.

19. A process for making one or more dehydration products from an aqueous sugar alcohols solution including one or more of the alcohols from pentoses and hexoses, comprising subjecting the aqueous sugar alcohols solution to an acid-catalyzed dehydration at an elevated temperature using a substituted sulfonic acid catalyst selected from the group consisting of dinonylnaphthalene sulfonic acid, 6-amino-m-toluenesulfonic acid, linear alkylbenzene sulfonic acid, and branched alkylbenzene sulfonic acid.

* * * * *